United States Patent
Berg et al.

(10) Patent No.: US 7,078,410 B2
(45) Date of Patent: Jul. 18, 2006

(54) 2-ARYLAMINO-PYRIMIDINES FOR THE TREATMENT OF GSK3-RELATED DISORDERS

(75) Inventors: Stefan Berg, Södertälje (SE); Ratan Bhat, Södertälje (SE); Sven Hellberg, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 38 days.

(21) Appl. No.: 10/468,605

(22) PCT Filed: Feb. 18, 2002

(86) PCT No.: PCT/SE02/00270

§ 371 (c)(1),
(2), (4) Date: Aug. 19, 2003

(87) PCT Pub. No.: WO02/066480

PCT Pub. Date: Aug. 29, 2002

(65) Prior Publication Data

US 2004/0106574 A1    Jun. 3, 2004

Related U.S. Application Data

(60) Provisional application No. 60/269,903, filed on Feb. 20, 2001.

(51) Int. Cl.
*C07D 471/04* (2006.01)
*A61K 31/437* (2006.01)

(52) U.S. Cl. ............... 514/269; 514/272; 544/321; 544/331

(58) Field of Classification Search ............ 514/54, 514/55, 56, 59, 269, 272; 544/321, 331
See application file for complete search history.

(56) References Cited

U.S. PATENT DOCUMENTS 5,521,184 A    5/1996   Zimmermann ............ 514/252
5,958,935 A    9/1999   Davis et al. ............. 514/275

FOREIGN PATENT DOCUMENTS

| EP | 0233461 | 8/1987 |
| EP | 0379979 | 8/1990 |
| WO | 0114375 | 3/2001 |
| WO | 0220495 | 3/2002 |

OTHER PUBLICATIONS

The Merck Manual, Fifteenth Edition, 1989, pp. 2145-2148, pp. 1380-1390; pp. 2141-2146.*
Kozlovsky et al, Am. J. Psychiatry, 2000, 157, 831-833.*
Imahori et al., J. Biochem. 121, 179-188 (1997).
Vijayaraghavan, et al. Biol. Reprod. 62/6, 1647-54 (2000).
Nikoulina, et al., Diabetes 49/2, 263-71 (2000).
Kozlovsky, et al., Am. J. Psychiatry 157/5, 831-3 (2000).
Gat, et al., Cell 95/5, 605-14 (1998).
Stambolic, et al., Curr. Biol. 6, 1664-1668 (1996).
Klein et al., PNAS 93, 8455-59 (1996).
Hoshi, et al., PNAS 93, 2719-2723 (1996).
Bhat, et al., PNAS 97, 11074-79 (2000).
Cotter, et al., NeuroReport 9, 1379-83 (1998).

* cited by examiner

*Primary Examiner*—Saojia A. Jiang
*Assistant Examiner*—Ganapathy Krishnan
(74) *Attorney, Agent, or Firm*—White & Case LLP

(57) ABSTRACT

An aqueous solution for prophylactic treatment of teats of lactating mammals, comprising as a first component at least partially deacetylated chitosan, or an acid addition salt thereof, in a concentration of up to about 2% by weight of chitosan, the solution having a pH of from about 4 to about 6.8, and said first component having a molecular weight such that the viscosity of the solution is less than about 50 mPas; and a method of prophylactic treatment of teats of lactating mammals.

10 Claims, No Drawings

2-ARYLAMINO-PYRIMIDINES FOR THE TREATMENT OF GSK3-RELATED DISORDERS

This application claims the benefit of Provisional Application No. 60/269,903 filed Feb. 20, 2001.

FIELD OF INVENTION

The present invention relates to a new use of pyrimidine derivatives, as a free base or a pharmaceutically acceptable salt thereof in the manufacture of a medicament in the treatment and/or prophylaxis of conditions associated with glycogen synthase kinase-3. The present invention further relates to a method of treatment and/or prophylaxis of conditions associated with glycogen synthase kinase-3, comprising administering to a mammal, including man in need of such prevention and/or prophylaxis a therapeutically effective amount of said pyrimidine derivatives. In addition, the present invention relates to new compounds suitable for the inhibition of glycogen synthase kinase-3.

BACKGROUND OF THE INVENTION

Glycogen synthase kinase 3 (GSK3) is a serine/threonine protein kinase composed of two isoforms (α and β), which are encoded by distinct genes but are highly homologous within the catalytic domain. GSK3 is highly expressed in the central and peripheral nervous system. GSK3 phosphorylates several substrates including tau, β-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies

AD is characterized by cognitive decline, cholinergic dysfunction and neuronal death, neurofibrillary tangles and senile plaques consisting of amyloid-β deposits. The sequence of these events in AD is unclear, but they are believed to be related. Glycogen synthase kinase 3β (GSK3β) or Tau (τ) phosphorylating kinase selectively phosphorylates the microtubule associated protein τ in neurons at sites that are hyperphosphorylated in AD brains. Hyperphosphorylated protein τ has lower affinity for microtubules and accumulates as paired helical filaments, which is the main component that constitutes neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalitic parkinsonism, progressive supranuclear palsy and Pick's Disease, and Niemann-Pick Disease. Addition of amyloid-β to primary hippocampal cultures results in hyperphosphorylation of τ and a paired helical-filaments-like state via induction of GSK3β activity, followed by disruption of axonal transport and neuronal death (Imahori and Uchida, J. Biochem. 121: 179–188, 1997). GSK3β preferentially labels neurofibrillary tangles and has been shown to be active in pre-tangle neurons in AD brains. GSK3 protein levels are also increased by 50% in brain tissue from AD patients. Furthermore, GSK3β phosphorylates pyruvate dehydrogenase, a key enzyme in the glycolytic pathway and prevents the conversion of pyruvate to acetyl-Co-A (Hoshi et al., PNAS 93:2719–2723, 1996). Acetyl-Co-A is critical for the synthesis of acetylcholine, a neurotransmitter with cognitive functions. Thus, GSK3β inhibition may have beneficial effects in progression as well as the cognitive deficits associated with Alzheimer's disease and other above-referred-to diseases.

Chronic and Acute Neurodegenerative Diseases

Growth factor mediated activation of the PI3K/Akt pathway has been shown to play a key role in neuronal survival. The activation of this pathway results in GSK3β inhibition. Recent studies (Bhat et. al., PNAS 97:11074–11079, 2000) indicate that GSK3β activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3β. Thus GSK3β inhibitors could be useful in attenuating the course of neurodegenerative diseases.

Bipolar Disorders (BD)

BD's are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664–1668, 1996; Klein and Melton; PNAS 93:8455–8459, 1996). Inhibition of GSK3β may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May;157 (5):831–3) found that GSK3β levels were 41% lower in the schizophrenic patients than in comparison subjects. This study indicates that schizophrenia involves neurodevelopmental pathology and that abnormal GSK3 regulation could play a role in schizophrenia. Furthermore, reduced β-catenin levels have been reported in patients exhibiting schizophrenia (Cotter et al., Neuroreport 9:1379–1383, 1998).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et. al. Diabetes 2000 February; 49(2):263–71). Inhibition of GSK3 increases the activity of glycogen synthase thereby decreasing glucose levels by its conversion to glycogen. GSK3 inhibition may therefor be of therapeutic relevance in the treatment of Type I and Type II Diabetes and Diabetic neuropathy.

Hair Loss

GSK3 phosphorylates and degrades β-catenin. β-catenin is an effector of the pathway for keratonin synthase. β-Mice expressing a stabilised β-catenin by mutation of sites phosphorylated by GSK3 undergo a process resembling de novo hair morphogenesis (Gat et al., Cell 1998 Nov. 25;95 (5): 605–14). The new follicles formed sebaceous glands and dermal papilla, normally established only in embryogenesis. Thus GSK3 inhibition may offer treatment for baldness.

Oral Contraceptives

Vijajaraghavan et al. (Biol Reprod 2000 June; 62 (6): 1647–54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

SUMMARY OF THE INVENTION

According to an aspect of the present invention, there is provided the use of a compound of formula (I) as a free base or a pharmaceutically acceptable salt thereof in the manufacture of a medicament for the treatment and/or prophylaxis of conditions associated with GSK3.

According to another aspect of the present invention, there is provided a method of treatment and/or prophylaxis of conditions associated with GSK3 comprising administering to a mammal, including man in need of such treatment and/or prophylaxis a therapeutically effective amount of a compound of formula (I) as a free base or a pharmaceutically acceptable salt thereof.

According to yet another aspect of the present invention, there is provided a pharmaceutical formulation for use in the treatment and/or prophylaxis of conditions associated with GSK3 comprising a therapeutically effective amount of a compound of formula (I) as a free base or a pharmaceutically acceptable salt thereof and conventional excipients.

In addition, the present invention relates to new compounds suitable for the inhibition of glycogen synthase kinase-3.

DETAILED DESCRIPTION OF THE INVENTION

It has now suprisingly been found that the group of pyrimidine derivatives as decribed below is well suited for inhibiting glycogen synthase kinase-3. The use of said glycogen synthase kinase-3 inhibitors are suitable in the treatment and/or prophylaxis of conditions associated with especially, dementia, Alzheimer's Disease, Parkinson's Disease, Frontotemporal dementia Parkinson's Type, Parkinson dementia complex of Gaum, HIV dementia, diseases with associated neurofibrillar tangle pathologies, amyotrophic lateral sclerosis, corticobasal degeneration, dementia pugilistica, Down's syndrome, Huntington's Disease, postencephelatic parkinsonism, progressive supranuclear palsy, Pick's Disease, Niemann-Pick's Disease, stroke, head trauma and other chronic neurodegenerative disorders, Bipolar Disease, affective disorders, depression, schizophrenia, cognitive disorders, Type I and Type II Diabetes and Diabetic neuropathy, hair loss and contraceptive medication.

In one aspect of the present invention use is made of a GSK3 inhibitor of the general formula (I) in the manufacturing of a medicament for the treatment and/or prophylaxis of conditions associated with glycogen synthase kinase-3,

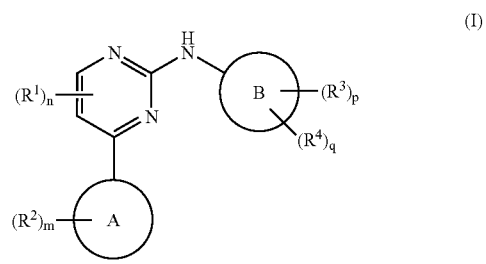

wherein:
Ring A is imidazo[1,2a]pyrid-3-yl or pyrazolo[2,3a]pyrid-3-yl;
$R^2$ is attached to a ring carbon and is selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{3-6}$cycloalkyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0, 1 or 2, $C_{1-6}$alkoxycarbonyl, N-($C_{1-6}$alkyl)sulphamoyl, N,N-($C_{1-6}$alkyl)$_2$sulphamoyl, phenyl, heterocyclic group, phenylthio or (heterocyclic group)thio; wherein any $C_{1-6}$alkyl, $C_{2-6}$alkenyl, $C_{2-6}$alkynyl, phenyl or heterocyclic group may be optionally substituted on carbon by one or more G; and wherein if said heterocyclic group contains an —NH— moiety that nitrogen may be optionally substituted by a group selected from Q;
m is 0, 1, 2, 3, 4 or 5; wherein the values of $R^2$ may be the same or different;
$R^1$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-2}$alkyl)$_2$amino, $C_{1-3}$alkanoylamino, N-($C_{1-3}$alkyl) carbamoyl, N,N-($C_{1-2}$alkyl)$_2$ carbamoyl, $C_{1-3}$ alkylS(O)$_a$ wherein a is 0, 1 or 2, N-($C_{1-3}$alkyl)sulphamoyl or N,N-($C_{1-3}$alkyl)$_2$sulphamoyl; wherein any $C_{1-2}$alkyl, $C_{1-3}$alkyl, $C_{2-3}$alkenyl or $C_{2-3}$alkynyl may be optionally substituted on carbon by one or more J;
n is 0, 1 or 2, wherein the values of $R^1$ may be the same or different;
Ring B is phenyl or phenyl fused to a $C_{5-7}$cycloalkyl ring;
$R^3$ is halo, nitro, cyano, hydroxy, amino, carboxy, carbamoyl, mercapto, sulphamoyl, $C_{1-6}$alkyl, $C_{2-6}$alkenyl or $C_{2-6}$alkynyl, $C_{1-6}$alkoxy;
p is 0, 1, 2, 3 or 4; wherein the values of $R^3$ may be the same or different;
$R^4$ is a group A-E-; wherein
A is selected from hydrogen, $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl; which $C_{1-6}$alkyl, phenyl, a heterocyclic group, $C_{3-8}$cycloalkyl, phenyl$C_{1-6}$alkyl, (heterocyclic group) $C_{1-6}$alkyl or $C_{3-8}$cycloalkyl$C_{1-6}$cycloalkyl may be optionally substituted on carbon by one or more D; and wherein if said heterocyclic group contains an —NH— moiety that nitrogen may be optionally substituted by a group selected from R;
E is a direct bond or —O—, —C(O)—, —OC(O)—, —C(O)O—, —N($R^a$)C(O)—, —C(O)N($R^a$)—, —N($R^a$)—, —S(O)$_r$—, —SO$_2$N($R^a$)— or —N($R^a$)

SO$_2$—; wherein R$^a$ is hydrogen or C$_{1-6}$alkyl optionally substituted by one or more D and r is 0, 1 or 2;

D is independently selected from oxo, halo, nitro, cyano, hydroxy, trifluoromethyl, trifluoromethoxy, amino, carboxy, carbamoyl, mercapto, sulphamoyl, C$_{1-6}$alkyl, C$_{2-6}$alkenyl, C$_{2-6}$alkynyl, C$_{1-1}$alkoxy, C$_{1-6}$alkanoyl, C$_{1-6}$alkanoyloxy, N-(C$_{1-6}$alkyl)amino, N,N-(C$_{1-6}$alkyl)$_2$ amino, C$_{1-6}$alkanoylamino, N-(C$_{1-6}$alkyl)carbamoyl, N,N-(C$_{1-6}$alkyl)$_2$carbamoyl, C$_{1-6}$alkylS(O)$_a$ wherein a is 0, 1 or 2, C$_{1-6}$alkoxycarbonyl, C$_{1-6}$alkoxycarbonylamino, benzyloxycarbonylamino, N-(C$_{1-6}$alkyl)sulphamoyl and N,N-(C$_{1-6}$alkyl)$_2$sulphamoyl; wherein any C$_{1-6}$alkyl, C$_{2-6}$alkenyl, C$_{2-6}$alkynyl or phenyl may be optionally substituted on carbon by one or more K;

q is 0, 1 or 2; wherein the values of R$^4$ may be the same or different; and wherein p+q≦5;

G, J and K are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and Q and R are independently selected from C$_{1-4}$alkyl, C$_{1-4}$alkanoyl, C$_{1-4}$alkylsulphonyl, C$_{1-4}$alkoxycarbonyl, carbamoyl, N-(C$_{1-4}$alkyl)carbamoyl, N,N-(C$_{1-4}$alkyl)carbamoyl, benzyl, benzyloxycarbonyl, benzoyl and phenylsulphonyl; as a free base or a pharmaceutically acceptable salt thereof.

Listed below are definitions of various terms used in the specification and claims to describe the present invention.

For the avoidance of doubt it is to be understood that where in this specification a group is qualified by 'hereinbefore defined' or 'defined hereinbefore' or 'defined above' the said group encompasses the first occurring and broadest definition as well as each and all of the preferred definitions for that group.

For the avoidance of doubt, the phrase "wherein any C$_{1-6}$alkyl is optionally substituted" and other such phrases also includes the possibility of optional substitution on other groups that contain a C$_{1-6}$alkyl group, for example a C$_{1-6}$alkoxy, C$_{1-6}$alkanoyl, C$_{1-6}$alkanoyloxy, N-(C$_{1-6}$alkyl) amino, N,N-(C$_{1-6}$alkyl)$_2$amino, C$_1$alkanoylamino, N-(C$_{1-6}$alkyl)carbamoyl, N,N-(C$_{1-6}$ alkyl)$_2$ carbamoyl, C$_{1-6}$ alkylS(O)$_a$ wherein a is 0, 1 or 2, C$_{1-6}$alkoxycarbonyl, C$_{1-6}$alkoxycarbonylamino, N-(C$_{1-6}$alkyl)sulphamoyl or a N,N-(C$_{1-6}$alkyl)$_2$sulphamoyl.

For the avoidance of doubt it is to be understood that in this specification 'C$_{1-6}$' means a carbon group having 1, 2, 3, 4, 5 or 6 carbon atoms.

In this specification, unless stated otherwise, the term "alkyl" includes both straight and branched chain alkyl groups. C$_{1-6}$alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl.

In this specification, unless stated otherwise, the term "C$_{3-6}$cycloalkyl" includes cyclopropyl, cyclobutyl, cyclopentyl and cyclohexyl. A similar convention applies to other radicals, for example "phenylC$_{1-6}$alkyl" includes phenylC$_{1-4}$ alkyl, benzyl, 1-phenylethyl and 2-phenylethyl.

The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclic group" is a saturated, partially saturated or unsaturated, mono or bicyclic ring containing 4 to 12 atoms of which at least one heteroatom is chosen from nitrogen, sulphur or oxygen, which may, unless otherwise specified, be carbon or nitrogen linked, wherein a —CH$_2$— group can optionally be replaced by a —C(O)—, a ring nitrogen atom may optionally bear a C$_{1-6}$alkyl group and form a quaternary compound or a ring nitrogen and/or sulphur atom may be optionally oxidised to form the N-oxide and or the S-sulfoxide or desulfione. Suitable examples of the term "heterocyclic group" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4pyridone, 1-isoquinolone, 2-pyrrolidone, 4-thiazolidone, pyridine-N-oxide and quinoline-N-oxide. Preferably a "heterocyclic group" is a saturated, partially saturated or unsaturated, mono or bicyclic ring containing 5 or 6 atoms of which at least one heteroatom is chosen from nitrogen, sulphur or oxygen, which may, unless otherwise specified, be, carbon or nitrogen linked, wherein a —CH$_2$— group can optionally be replaced by a —C(O)—, a ring nitrogen atom may optionally bear a C$_{1-6}$alkyl group and form a quaternary compound or a ring nitrogen and/or sulphur atom may be optionally oxidised to form the N-oxide and or the S-sulfoxide or desulfione.

A suitable value for phenyl fused to a C$_{5-7}$cycloalkyl ring is indanyl or tetralinyl.

An example of "C$_{1-6}$alkanoyloxy" is acetoxy. Examples of "C$_{1-6}$alkoxycarbonyl" include C$_{1-4}$alkoxycarbonyl, methoxycarbonyl, ethoxycarbonyl, n- and t-butoxycarbonyl. Examples of "C$_{1-6}$alkoxy" include C$_{1-3}$alkoxy, methoxy, ethoxy and propoxy. Examples of "C$_{1-6}$alkanoylamino" include C$_{1-3}$alkanoylamino, formamido, acetamido and propionylamino. Examples of "C$_{1-6}$alkylS(O)$_a$ wherein a is 0, 1 or 2" include C$_{1-4}$alkylsulphonyl, C$_{1-3}$alkylS(O)$_a$, methylthio, ethylthio, methylsulphinyl, ethylsulphinyl, mesyl and ethylsulphonyl. Examples of "C$_{1-6}$alkanoyl" include C$_{1-4}$alkanoyl, C$_{1-3}$alkanoyl, propionyl and acetyl. Examples of "N-C$_{1-6}$alkylamino" include N-(C$_{1-3}$alkyl)amino, methylamino and ethylamino. Examples of "N,N-(C$_{1-6}$alkyl)$_2$ amino" include N,N-(C$_{1-2}$alkyl)$_2$amino, di-N-methylamino, di-(N-ethyl)amino and N-ethyl-N-methylamino. Examples of "C$_{2-6}$alkenyl" are C$_{2-3}$alkenyl, vinyl, allyl and 1-propenyl. Examples of "C$_{2-6}$alkynyl" are C$_{2-3}$alkynyl, ethynyl, 1-propynyl and 2-propynyl. Examples of "N-(C$_{1-6}$alkyl)sulphamoyl" are N-(C$_{1-3}$alkyl)sulphamoyl, N-(methyl)sulphamoyl and N-(ethyl)sulphamoyl. Examples of "N-(C$_1$alkyl)$_2$sulphamoyl" are N,N-(C$_{1-3}$alkyl)$_2$sulphamoyl, N,N-(dimethyl)sulphamoyl and N-(methyl)-N-(ethyl)sulphamoyl. Examples of "N-(C$_{1-6}$alkyl)carbamoyl" are N-(C$_{1-6}$ alkyl)carbamoyl, N-(C$_{1-3}$alkyl)carbamoyl, methylaminocarbonyl and ethylaminocarbonyl. Examples of "N,N-(C$_{1-6}$alkyl)$_2$carbamoyl" are N,N-(C$_{1-4}$alkyl)carbamoyl, N,N-(C$_{1-2}$alkyl)$_2$carbamoyl, dimethylaminocarbonyl and methylethylaminocarbonyl. Examples of "C$_{5-7}$cycloalkyl ring" are cyclopentyl and cyclohexyl. Examples of "(heterocyclic group)C$_{1-6}$alkyl" include pyridylmethyl, 3-morpholinopropyl and 2-pyrimid-2-ylethyl. Examples of "(heterocyclic group)thio" include thienylthio and pyridylthio. Examples of "$C_{3-8}$cycloalkyl" include cyclopropyl and cyclohexyl. Examples of "$C_{3-8}$cycloalkyl$C_{1-6}$cycloalkyl" include cyclopropylmethyl and 2-cyclohexylpropyl. Examples of "$C_{1-6}$alkoxycarbonylamino" include methoxycarbonylamino and t-butoxycarbonylamino.

A suitable pharmaceutically acceptable salt of a compound of the invention is, for example an inorganic or organic acid, for example hydrochloric, hydrobromic, sulphuric, phosphoric, trifluoroacetic, citric or maleic acid. In addition a suitable pharmaceutically acceptable salt of a compound of the invention is for example an alkali metal salt, an alkaline earth metal salt, an ammonium salt or a salt with an organic base which provides a physiologically-acceptable cation.

The compounds of the formula (a) may be administered in the form of a pro-drug, which is metabolised in vivo to give a compound of the formula (I). Examples of pro-drugs include in vivo hydrolysable esters of a compound of the formula (I) having a carboxy or hydroxy group.

Some compounds of the formula (I) may have chiral centres and/or geometric isomeric centres (E- and Z-isomers), and it is to be understood that the invention encompasses all such optical, diastereoisomeric and geometric isomers that possess GSK3 inhibitory activity.

The invention also relates to any and all tautomeric forms of the compounds of the formula (I) that possess GSK3 inhibitory activity.

Another aspect of the invention relates to novel compounds, which are;
2-(4-Fluoro-3-methylanilino)-4-(imidazo[1,2a]pyrid-3-yl)pyrimidine,
2-(4-Cyanoanilino)-4-(imidazo[1,2a]pyrid-3-yl)pyrimidine,
2-(4-Chloroanilino)-4-(imidazo[1,2a]pyrid-3-yl)pyrimidine,
2-Anilino-4-(2-methylimidazo[1,2a]pyrid-3-yl)pyrimidine,
2-[4-(Pyrimid-2-ylaminosulphonyl)anilino]-4-(imidazo[1,2a]pyrid-3-yl)pyrimidine,
2-(4-Carbamoylanilino)-4-(imidazo[1,2a]pyrid-3-yl)pyrimidine,
2-(3-Cyanoanilino)-4-(imidazo[1,2a]pyrid-3-yl)pyrimidine,
2-(3,5-Difluoroanilino)-4-(imidazo[1,2a]pyrid-3-yl)pyrimidine,
2-(3-Chloroanilino)-4-(imidazo[1,2a]pyrid-3-yl)pyrimidine,
2-[4-(N,N-Dimethyl-carbamoyl)anilino]-4-(imidazo[1,2a]pyrid-3-yl)pyrimidine,
2-(4-Mesylanilino)-4-(imidazo[1,2a]pyrid-3-yl)pyrimidine and
2-(3-Sulphamoylanilino)-4-(imidazo[1,2a]pyrid-3-yl)pyrimidine, as a free base or pharmaceutically acceptable salt thereof.

The present invention also relates to the use of the above listed compounds in the manufacture of a medicament for the treatment and/or prophylaxis of conditions associated with glycogen synthase kinase-3 inhibition.

METHODS OF PREPARATION

Another aspect of the present invention provides a process for preparing a compound of formula I as a free base or a pharmaceutically acceptable salt thereof. The process, (wherein $R^1$, $R^2$, $R^3$, $R^4$, X, Ring A, Ring C, Ring D, m, p, q and n are, unless otherwise specified, are as defined in formula I and Ring B is a pyrimidine or a pyridine wherein P is N or CR$^1$), comprising:

a) reacting of a pyrimidine or a pyridine of formula II:

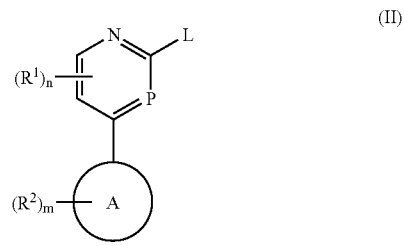

wherein L is an amine or a leaving group; with a compound of formula III wherein L is an amine or a leaving group:

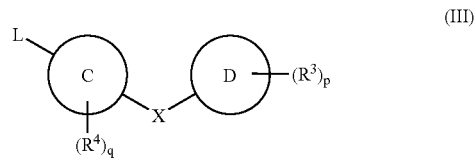

b) reacting a pyrimidine or a pyridine of formula IV:

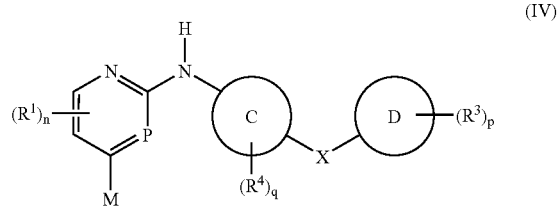

with a compound of the formula V:

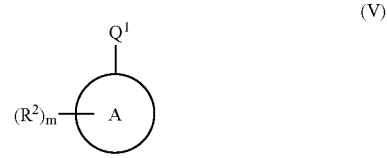

wherein one of M and Q$^1$ is a leaving group E and the other is a metallic group Y; or c) when P is N, reacting a compound of formula VI:

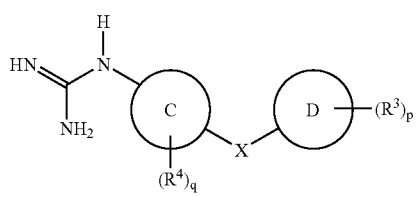

with a compound of formula VII:

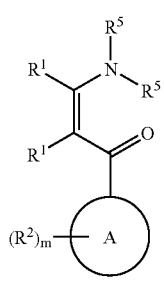

wherein $R^5$ is $C_{1-6}$alkyl and $R^1$ is as defined above;

and thereafter, if necessary:
i) converting a compound of the formula I into another compound of the formula I e.g. reduction of X when X is CO to $C(OR^5)R^6$ wherein $R^5=R^6$=hydrogen.
ii) removing any protecting groups; and
iii) forming a free base or a pharmaceutically acceptable salt or in vivo hydrolysable ester thereof.

L is defined as an amino group or leaving groups. Suitable leaving groups are for example, a halo, sulphonyloxy group or a thio ether, for example a chloro, bromo, methanesulphonyloxy or a toluenesulphonyloxy group or a thiomethyl ether. One of the L is an amino group and the other is a leaving group.

A suitable leaving group E is, for example, a halo or sulphonyloxy group, for example a bromo, iodo or trifluoromethylsulphonyloxy group.

A suitable metallic group Y, is, for example, copper, lithium, an organoboron reagent such as $B(OH)_2$, $B(OPr^i)_2$ or $B(Et)_2$, or an organotin compound such as $SnBu_3$, an organosilicon compound such as $Si(Me)F_2$, an organozirconium compound such as $ZrCl_3$, an organoaluminium compound such as $AlEt_2$, an organomagnesium compound such as MgBr, an organozinc compound such as ZnCl or an organomercury compound such as HgBr.

Suitable reaction conditions for the above reactions are as follows:
a) A compound of formula II and a compound of formula III may be reacted together:
i) in the presence of a suitable solvent for example a ketone such as acetone or an alcohol such as ethanol or butanol or an aromatic hydrocarbon such as toluene or N-methyl pyrrolidine, optionally in the presence of a suitable base for example an inorganic base such as potassium carbonate or an organic base such as triethyl amine or sodium bis(trimethylsilyl)amide, or optionally in the presence of a suitable acid for example an inorganic acid such as hydrochloric acid or sulphuric acid, or an organic acid such as acetic acid or formic acid or a suitable Lewis acid and at a temperature in the range of 0° C. to reflux, preferably at reflux; or
ii) in the presence of a suitable palladium catalyst such as $PdX_2$, $L^a_2Pd(0)$ or $L^a_2PdX_2$, where X stands for a halogen such as chlorine or bromine and $L^a$ stands for a suitable ligand such as triphenylphosphine, tri-o-tolylphosphine, trifurylphosphine, triphenylarsine or dibenzylidenacetone and with or without an addition of a ligand $L^b$ such as triphenylphosphine, tri-o-tolylphosphine, trifurylphosphine, 2,2'-bis(diphenylphosphino)-1,1'-binaphthalene (either as a racemate or as an enantiomer) or triphenylarsine in an suitable solvent such as dioxane, tetrahydrofuran, toluene, benzene, N,N-dimethylformamide or xylene in the presence of a suitable base such as cesium carbonate, sodium tert-butoxide or lithium bis(trimethylsilyl)amide and the reaction may occur at a temperature between +20° C. and +150° C.

A compound of the formula II may be prepared according to SCHEME I

SCHEME I

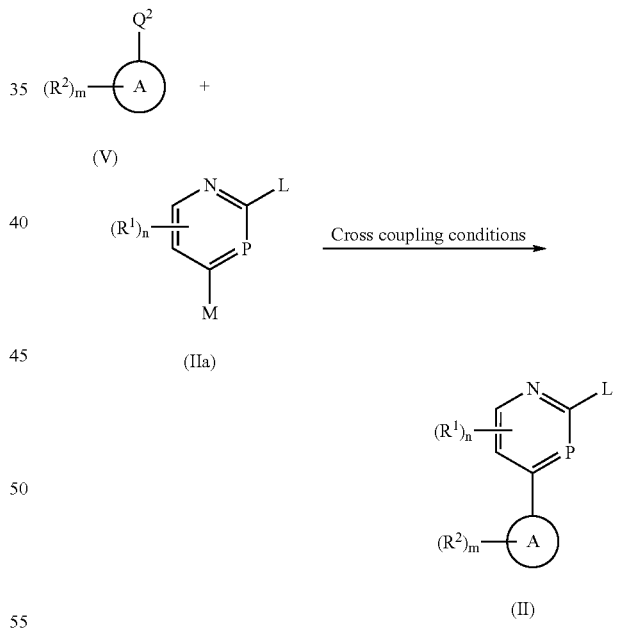

wherein one of M and $Q^2$ is a leaving group E as defined above and the other is a metallic group Y as defined above and L is as defined above.

Cross coupling conditions are well known in the art. Suitable conditions include, for example, those described under b) below.

Compounds of the formula II where Ring A is imidazo[1,2a]pyrid-3-yl and when P is N, may also be prepared according to SCHEME II.

SCHEME II
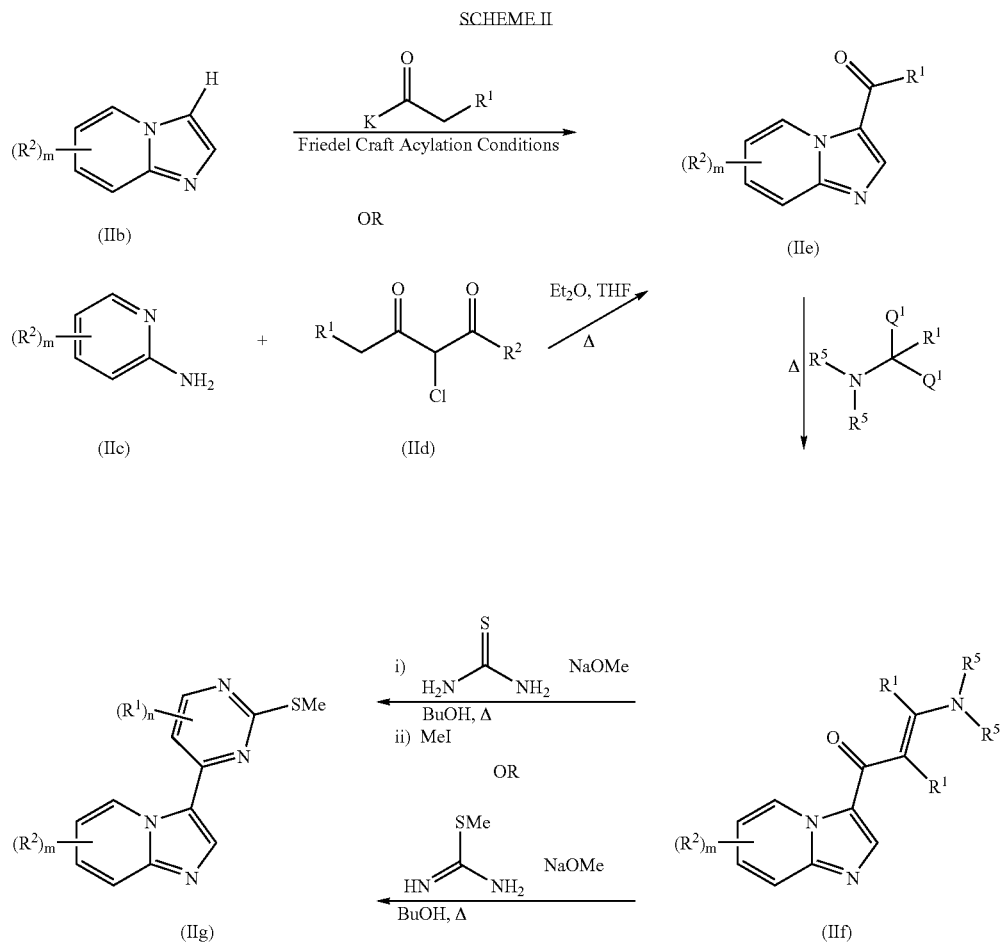
K is a suitable leaving group (for example $C_{1-6}$alkanoyloxy), $R^1$ and $R^2$ are as defined above, m is 0, 1, 2, 3 or 4; $Q^1$ is a suitable leaving group (for example $C_{1-6}$alkoxy) and $R^5$ is as defined above.
Where Ring A is pyrazolo[2,3a]pyrid-3-yl compounds of the formula II and when P is N, may also be prepared according to SCHEME III.
SCHEME III
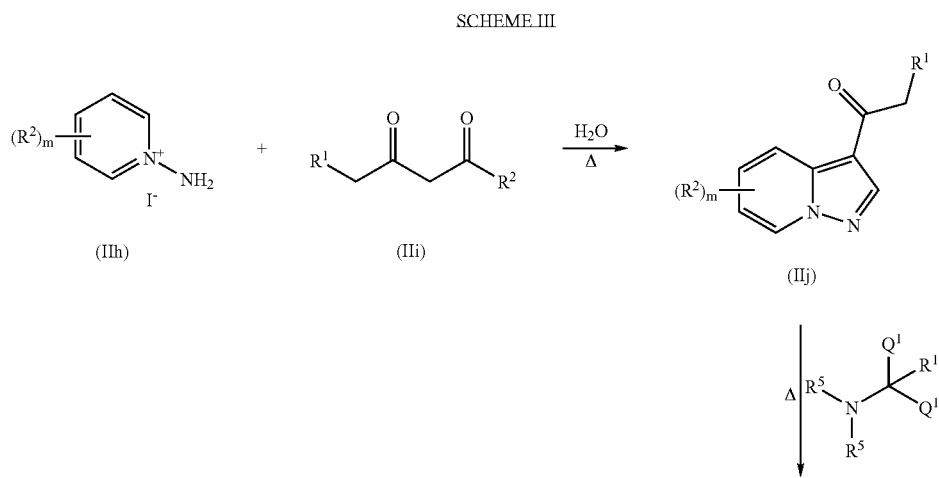

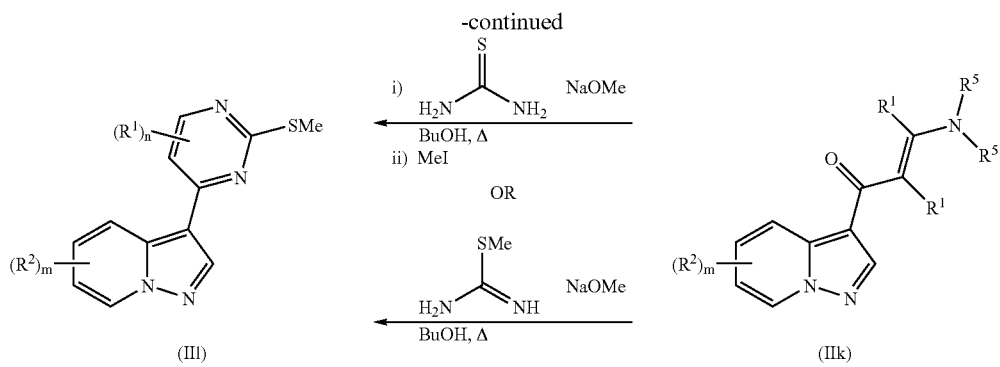

wherein $Q^1$, $R^1$, $R^2$ and $R^5$ are as defined above.

Compounds of formula IIf or IIk may be further modified to produce compounds of formula IIn:

SCHEME IV

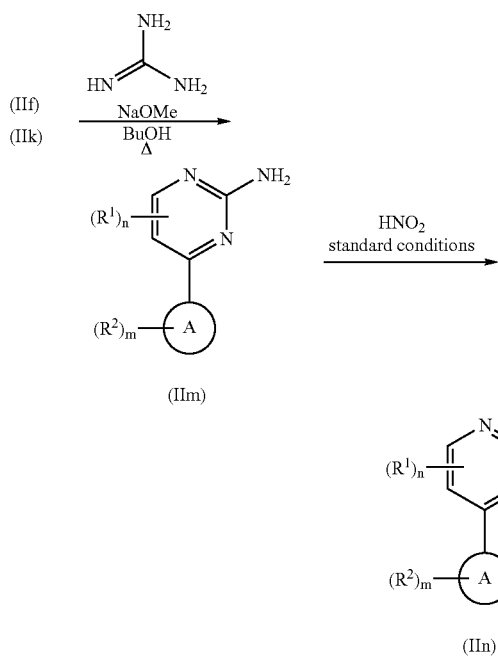

It will be appreciated by those skilled in the art that compounds of formula IIn may be additionally modified by standard functional group modification reactions known in the art to produce compounds of formula II where L is as defined above.

Compounds of formula III, where X is —CO—, may be prepared according to SCHEME V,

SCHEME V

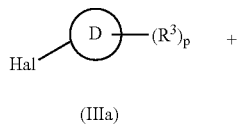

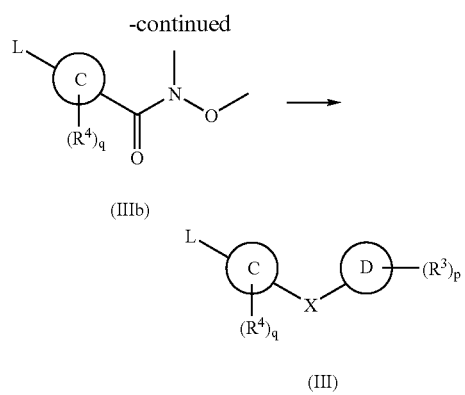

by a metal-halogen exchange reaction, in an appropriate anhydrous solvent such as tetrahydrofuran or diethyl ether using a suitable alkyl-lithium or metal e.g. butyllithium, lithium or magnesium turnings, of a compound of formula IIIa, wherein Hal is Cl, Br or I, followed by reaction with a compound of formula IIIb, wherein L is as defined above. The reaction may be performed at a reaction temperature within the range of −78° C. to is room temperature.

Compounds of formula IIa, IIb, IIc, IId, IIh, IIi, IIIa and IIIb are commercially available compounds, or they are known in the literature, or they are prepared by standard processes known in the art.

b) Compounds of formula IV and compounds of formula V may be reacted together under standard cross coupling conditions. Examples of these are in the presence of a catalyst, for example, a metallic catalyst such as tetrakis (triphenylphosphine)palladium(0), palladium(II) chloride, palladium(II) bromide, nickel(II) chloride, nickel(II) bromide or bis(triphenylphosphine)nickel(II) chloride, in the presence of a suitable inert solvent or diluent, for example tetrahydrofuran, 1,4-dioxan, 1,2-dimethoxyethane, benzene, toluene, xylene, methanol or ethanol. The reaction is preferably conducted in the presence of a suitable base such as, for example, sodium carbonate or potassium carbonate, pyridine, 4-dimethylaminopyridine, triethylamine or morpholine, and conveniently at a temperature in the range of, for example 10 to 250° C., preferably in the range of 60 to 120° C.

Compounds of formula IV may be prepared according to SCHEME VI

One of the L is an amino group and the other L is a leaving group.

SCHEME VI

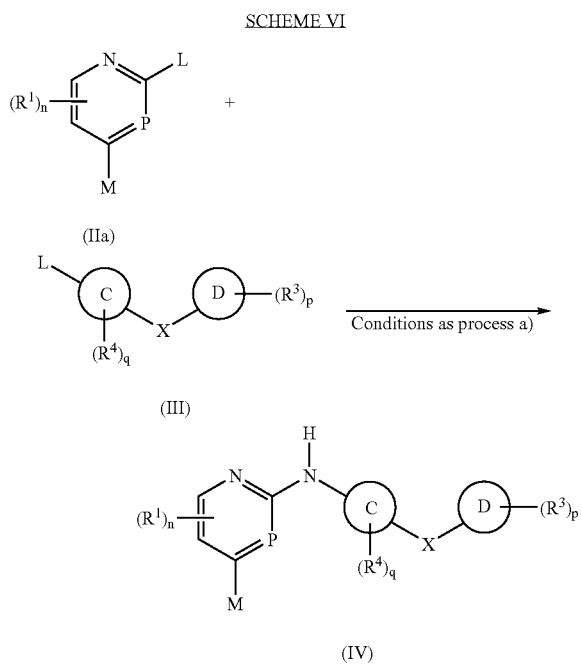

Compounds of formula V are commercially available compounds, or they are known in the literature, or they are prepared by standard processes known in the art.

c) Compounds of formula VI and compound of formula VII are reacted together in a suitable solvent such as NV-methylpyrrolidinone or butanol at a temperature in the range of 100 to 200° C., preferably in the range of 150 to 170° C. The reaction is preferably conducted in the presence of a suitable base such as, for example, sodium methoxide or potassium carbonate.

Compounds of formula VI and VII are commercially available compounds, or they are known in the literature, or they are prepared by standard processes known in the art, or compounds of formula VII may be prepared by a process similar to that described for IIf and IIk hereinabove.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl. It will also be appreciated that in some of the reactions mentioned herein it may be necessary/desirable to protect any sensitive groups in the compounds. The instances where protection is necessary or desirable, suitable methods for protection are known to those skilled in the art. Conventional protecting groups may be used in accordance with standard practice (for illustration see T. W. Green, P. G. M. Wutz, Protective Groups in Organic Synthesis, Wiley Interscience, 1999). The protecting groups may be removed at any convenient stage in the synthesis using conventional techniques well known in the chemical art.

EXAMPLES

The invention will now be illustrated by the following non-limiting examples in which, unless stated otherwise:

(i) temperatures are given in degrees Celsius (° C.); operations were carried out at a temperature in the range of 18–25° C., i.e. room or ambient temperature, if not otherwise indicated;

ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;

(iii) chromatography means flash chromatography on silica gel; thin layer chromatography (TLC) was carried out on silica gel plates; where a silica Bond Elut column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI", "Mega Bond Elut" is a trademark;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values given in parts per million (ppm) relative to tetramethylsilane (TMS) as an internal standard, determined at 300 MHz or 400 Mhz instrument using perdeuterio dimethyl sulphoxide (DMSO-d6) or deuterio chloroform (CDCl$_3$) as solvent unless otherwise indicated;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a LC-MS or a direct exposure probe; where indicated ionization was effected by electron impact (EI), fast atom bombardment (FAB) or electrospray (ESP), if not otherwise indicated; values for m/z are given; generally, only ions which indicate the parent mass are reported;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example if not anything else is indicated;
(xiii) the following abbreviations have been used:

| | |
|---|---|
| NMP | 1-methyl-2-pyrrolidinone; |
| DMF | N,N-dimethylformamide; |
| DMFDMA | N,N-dimethylformamidedimethylacetyl; |
| DMSO | dimethylsulphoxide; |
| THF | tetrahydrofuran; and |
| EA | elemental analysis. |

Example 1

2-(3-Chloroanilino)-4-(2-methylimidazo[1,2a]pyrid-3-yl)pyrimidine

Sodium hydride (236 mg of a 60% suspension in mineral oil, 5.9 mmol) was added to a solution of 3-chloroaniline (496 ml, 4.7 mmol) in NMP (10 ml) under nitrogen. The mixture was stirred for 30 minutes at ambient temperature and a solution of 4-(2-methylimidazo[1,2a]pyrid-3-yl)-2-methylthiopyrimidine (Method 1) (600 mg, 2.3 mmol) in NMP (2 ml) was added. The mixture was heated at 150° C. for 3 hours. The reaction mixture was allowed to cool, diluted with water and extracted with ethyl acetate. The combined extracts were dried and the volatiles removed by evaporation. The residue was purified by chromatography eluting with ethyl acetate/hexane (1:1) increasing in polarity to ethyl acetate/methanol (97:3). The purified product was triturated with diethylene ether and hexane, collected by filtration and dried to give the title compound (159 mg, 21% yield). NMR: 2.62 (s, 3H), 6.98–7.04 (m, 2H), 7.12 (d, 1H), 7.25 (dd, 1H), 7.42 (dd, 1H), 7.59–7.64 (m, 2H), 8.02 (s, 1H), 8.55 (d, 1H), 9.72 (d, 1H), 9.84 (s, 1H).

Examples 2–12

Following the procedure of Example 1 and using the appropriate starting materials the following compounds were prepared,

| Ex | Compound | NMR | m/z [MH]+ |
|---|---|---|---|
| 2 | 2-(4-Sulphamoylanilino)-4-(2-methylimidazo[1,2a]pyrid-3-yl)pyrimidine | 2.64(s, 3H), 7.05(dd, 1H), 7.15–7.20 (m, 3H), 7.44(dd, 1H), 7.64(d, 1H), 7.74(d, 2H), 7.92(d, 2H), 8.68(d, 1 H), 9.75(d, 1H) | 381 |
| 3[1] | 2-Anilino-4-(2-methylimidazo[1,2a]pyrid-3-yl)pyrimidine | 2.64(s, 3H), 6.92–7.00(m, 2H), 7.08 (d, 1H), 7.30(dd, 1H), 7.40(dd, 1H), 7.60(d, 1H), 7.72(d, 2H), 8.50(d, 1 H), 9.60(s, 1H), 9.75(d, 1H) | 302 |
| 4 | 2-(4-Chloroanilino)-4-(2-methylimidazo[1,2a]pyrid-3-yl)pyrimidine | 2.75(s, 3H), 6.82(dd, 1H), 7.01(d, 1 H), 7.22(br s, 1H), 7.30(m, 3H), 7.60 (m, 2H), 8.47(d, 1H), 9.53(d, 1H) | 336 |
| 5[1] | 2-(3-Chloroanilino)-4-(imidazo[1,2a]pyrid-3-yl)pyrimidine | 7.02(d, 1H), 7.12(dd, 1H), 7.30(dd, 1 H), 7.42(d, 1H), 7.50(dd, 1H), 7.60 (d, 1H), 7.75(d, 1H), 8.00(s, 1H), 8.48(d, 1H), 8.61(s, 1H), 9.82(s, 1H) | 322 |
| 6[1] | 2-(3,4-Dichloroanilino)-4-(imidazo[1,2a]pyrid-3-yl)pyrimidine | 7.15(dd, 1H), 7.50(dd, 2H), 7.58(d, 1 H), 7.65(dd, 1H), 7.78(d, 1H), 8.22 (d, 1H), 8.50(d, 1H), 8.62(s, 1H), 9.95(s, 1H) | |
| 7 | 2-(4-Sulphamoylanilino)-4-(imidazo[1,2a]pyrid-3-yl)pyrimidine | 7.20(d, 3H), 7.55(d, 2H), 8.80(d, 3 H), 8.95(d, 2H), 8.50(d, 1H), 8.68(s, 1H), 10.05(s, 1H), 10.10(d, 1H) | 367 |
| 8[1] | 2-(3-Chloro-4-fluoroanilino)-4-(imidazo[1,2a]pyrid-3-yl)pyrimidine | 7.14(dd, 1H), 7.32–7.55(m, 3H), 7.60 (dd, 1H), 7.78(d, 1H), 8.10(dd, 1H), 8.48(d, 1H), 8.62(s, 1H), 9.82(s, 1H) | 340 |
| 9 | 2-(2-Chloroanilino)-4-(imidazo[1,2a]pyrid-3-yl)pyrimidine | 7.08(dd, 1H), 7.17(d, 1H), 7.37(m, 2 H), 7.48(dd, 1H), 7.51(br s, 1H), 7.62 (d, 1H), 7.76(d, 1H), 8.30(s, 1H), 8.40(m, 1H), 9.81(d, 1H), 9.94(dd, 1H) | 322 |
| 10 | 2-(2-Chloro-4-methylanilino)-4-(imidazo[1,2a]pyrid-3-yl)pyrimidine | 2.38(s, 3H), 6.91(dd, 1H), 7.14(d, 1 H), 7.28(br s, 1H), 7.38(m, 2H), 7.61 (s, 1H), 7.73(d, 1H), 8.16(d, 1H), 8.28(s, 1H), 8.40(d, 1H), 9.78(d, 1 H) | 336 |

-continued

| Ex | Compound | NMR | m/z [MH]+ |
|---|---|---|---|
| 11[1] | 2-[4-(3,5-Dioxapiperidin-1-yl) sulphonylanilino]-4-(imidazo [1,2a]pyrid-3-yl)pyrimidine | 4.87(s, 2H), 5.20(s, 4H), 7.16(dd, 1 H), 7.51(d, 2H), 7.75(d, 1H), 7.83(d, 2H), 7.98(d, 2H), 8.50(d, 1H), 8.64 (s, 1H) | 439 |
| 12[1,2] | 2-[4-(2-Diethylaminoethoxy) anilino]-4-(imidazo[1,2a]pyrid-3-yl)pyrimidine | 0.98(t, 6H), 2.50–2.62(m, 4H), 2.78–2.82(m, 2H), 4.00(t, 2H), 6.84 (dd, 2H), 7.08(dd, 1H), 7.38(d, 1H), 7.48(dd, 1H), 7.60(s, 2H), 7.75(d, 1 H), 8.38(d, 1H), 8.59(s, 1H), 9.42(s, 1H) | 403 |

[1] Sodium bis (trimethylsilyl) amide (1 M solution in THF) was used in stead of sodium hydride.
[2] The product was purified by chromatography, eluting with dichloromethane/methanol (100:0 increasing to 80:20), triturated with diethylene ether andHexane and collected by filtration.

Example 13

2-[4-(3-Dimethylamino-2-hydroxypropoxy)anilino]-4-(imidazo[1,2a]pyrid-3-yl)pyrimidine A mixture of 4-(3-dimethylamino-2-hydroxypropoxy) aniline (497 mg, 1.76 mmol) (Method 11) and cyanamide (185 mg, 4.4 mmol) in NMP (1 ml) was heated at 160° C. for 30 minutes. A mixture of 3-(3-dimethylaminoprop-2-en-1-oyl)imidazo[1,2a]pyridine (Method 5) (400 mg, 1.76 mmol) and sodium methoxide (183 mg, 3.5 mmol) in 1-butanol (10 ml) was then added and the mixture heated at reflux for 3 hours. The mixture was allowed to cool and the residue was purified by chromatography, eluting with ethyl acetate/methanol (97:3 increasing in polarity to 90:10) to give the title compound (30 mg, 4% yield). NMR: 2.35 (s, 6H), 2.40–2.63 (m, 2H), 3.82–4.02 (m, 3H), 6.90 (d, 2H), 7.06 (dd, 1H), 7.30 (d, 1H), 7.50 (dd, 1H), 7.59 (s, 2H), 7.74 (d, 1H), 8.38 (d, 1H), 8.58 (s, 1H), 9.42 (s, 1H); m/z: 405 [MH]+.

Examples 14–15

Following the procedure of Example 13 and using the appropriate starting materials the following compounds were prepared,

| Ex | Compound | NMR | m/z [MH]+ |
|---|---|---|---|
| 14[1] | 2-[4-(3-Dimethylamino-2-Hydroxypropoxy)anilino]-4-(2-methylpyrazolo[2,3a]pyrid-3-yl)pyrimidine | 2.20(s, 6H), 2.26–2.45(m, 2H), 2.65 (s, 3H), 3.80–3.95(m, 3H), 4.80(s, 1 H), 6.88(d, 2H), 7.00(d, 2H), 7.38 (dd, 1H), 7.60(d, 2H), 8.38(d, 1H), 8.44(d, 1H), 8.65(d, 1H), 9.21(s, 1H) | 419 |
| 15[2] | 2-[4-(3-Dimethylamino-2-Hydroxypropoxy)anilino]-4-(2-methylimidazo[1,2,a]pyrid-3-yl)pyrimidine | 2.63(s, 3H), 2.80(s, 6H), 3.12–3.26 (m, 2H), 4.27(br s, 1H), 5.93(br s, 1 H), 6.90–7.04(m, 4H), 7.40(t, 1H), 7.60(dd, 2H), 8.45(d, 1H), 9045(s, 1H), 9.73(d, 1H) | 419 |

[1] Product was purified by chromatography eluting with dichloromethane/hexane (1:1) increasing in polarity to dichloromethane/methanol/triethylamine (96:4:0.5).
[2] Product was purified by chromatography eluting with dichloromethane/methanol/triethylamine (96:4:0.5) and recrystallized from acetonitrile/methanol.

Examples 16–36

The following examples were prepared, purified and characterised by the following generic method:

Sodium bis(trimethylsilyl)amide (2.05 ml of a 1M solution in THF, 2.05 mmol) was added to a solution of the aniline (1.65 mmol) in NMP (1.5 ml) under nitrogen. The mixture was stirred for 30 minutes at ambient temperature and a solution of 4-(imidazo[1,2a]pyrid-3-yl)-2-methylthiopyrimidine (Method 4) (200 mg, 0.83 mmol) in NMP (1 ml) was added. The reaction mixture was heated at 150° C. for 2.5 hours. The solvent and volatiles were removed by evaporation and the residue was purified by chromatography eluting with ethyl acetate, then ethyl acetate/methanol (97:3) and finally ethyl acetate/methanol (97:3). The reaction products were characterised by HPLC on a 4.6 mm×10 cm Hichrom RPB 100A column eluting water/acetonitrile/formic acid (95:5:0.1 for 1.5 minutes then on a 10 minute gradient to 5:95:0.1) with a flow rate of 1.0 ml/minute, detecting at 254 nm (bandwidth 10 nm).

| Ex | Compound | HPLC Ret Time(mins) | M/z [MH]+ |
|---|---|---|---|
| 16 | 2-Anilino-4-(imidazo[1,2a]pyrid-3-yl)pyrimidine | 7.26 | 288 |
| 17 | 2-(2-Fluoroanilino)-4-(imidazo[1,2a]pyrid-3-yl)pyrimidine | 7.26 | 306 |
| 18 | 2-(3-Bromoanilino)-4-(imidazo[1,2a]pyrid-3-yl)pyrimidine | 8.30 | 368 |
| 19 | 2-(3-Fluoroanilino)-4-(imidazo[1,2a]pyrid-3-yl)pyrimidine | 7.70 | 306 |
| 20 | 2-(3-Methoxyanilino)-4-(imidazo[1,2a]pyrid-3-yl)pyrimidine | 7.39 | 318 |
| 21 | 2-(3-Methylthioanilino)-4-(imidazo[1,2a]pyrid-3-yl)pyrimidine | 7.98 | 334 |
| 22 | 2-(3-Acetylanilino)-4-(imidazo[1,2a]pyrid-3-yl)pyrimidine | 7.13 | 330 |
| 23 | 2-(3-Ethylanilino)-4-(imidazo[1,2a]pyrid-3-yl)pyrimidine | 8.11 | 316 |
| 24 | 2-(4-Fluoroanilino)-4-(imidazo[1,2a]pyrid-3-yl)pyrimidine | 7.47 | 306 |
| 25 | 2-(4-Chloroanilino)-4-(imidazo[1,2a]pyrid-3-yl)pyrimidine | 8.15 | 322 |
| 26 | 2-(4-Methoxyanilino)-4-(imidazo[1,2a]pyrid-3-yl)pyrimidine | 7.02 | 318 |
| 27 | 2-(4-Benzyloxyanilino)-4-(imidazo[1,2a]pyrid-3-yl)pyrimidine | 8.65 | 394 |
| 28 | 2-[4-(Anilinosulphonyl)anilino]-4-(imidazo[1,2a]pyrid-3-yl)pyrimidine | 7.79 | 443 |
| 29 | 2-(4-Mesylanilino)-4-(imidazo[1,2a]pyrid-3-yl)pyrimidine | 6.84 | 366 |
| 30 | 2-(4-Methylthioanilino)-4-(imidazo[1,2a]pyrid-3-yl)pyrimidine | 7.89 | 334 |
| 31 | 2-(4-Methylanilino)-4-(imidazo[1,2a]pyrid-3-yl)pyrimidine | 7.65 | 302 |
| 32 | 2-(3-Sulphamoylanilino)-4-(imidazo[1,2a]pyrid-3-yl)pyrimidine | 6.30 | 367 |
| 33 | 2-[4-(Pyrimid-2-ylaminosulphonyl)anilino]-4-(imidazo[1,2a]pyrid-3-yl)pyrimidine | 6.72 | 445 |
| 34 | 2-(4-Phenoxyanilino)-4-(imidazo[1,2a]pyrid-3-yl)pyrimidine | 8.86 | 380 |
| 35 | 2-(3-Methylanilino)-4-(imidazo[1,2a]pyrid-3-yl)pyrimidine | 7.63 | 302 |
| 36 | 2-(Indan-5-ylamino)-4-(imidazo[1,2a]pyrid-3-yl)pyrimidine | 8.20 | 328 |

Example 37

2-(3-Chloroanilino)-4-(2,5-dimethylimidazo[1,2a]pyrid-3-yl)pyrimidine

2-Methylthio-4-(2,5-dimethylimidazo[1,2a]pyrid-3-yl)pyrimidine (Method 14) (200 mg, 0.74 mmol) was added to a solution of 3-chloroaniline (0.16 ml, 1.48 mmol) and sodium hydride (60 mg, 1.48 mmol) in NMP (1 ml) under nitrogen. The mixture was heated at 150° C. for 4 hours and then allowed to cool. The crude reaction mixture was loaded onto a Bond Elut column eluting with dichloromethane to remove the NMP and then with dichloromethane/methanol/methylamine (75:20:5) to elute the product. The product was further purified by chromatography eluting with ethyl acetate/hexane (8:2) and then ethyl acetate to give the title compound (22 mg, 9% yield). NMR: 2.27 (s, 3H), 2.61 (s, 3H), 7.01 (d, 1H), 7.12 (d, 1H), 7.30 (m, 2H), 7.56 (d, 1H), 7.62 (d, 1H), 8.57 (d, 1H), 9.41 (s 1H), 9.83 (s, 1H); m/z: 350 [MH]+.

Example 38

Following the procedure of Example 37 and using the appropriate starting materials the following compound was prepared,

| Ex | Compound | NMR | m/z [MH]+ |
|---|---|---|---|
| 38 | 2-(3-Chloroanilino)-4-(2-methylpyrazolo[2,3a]pyrid-3-yl)pyrimidine | 2.64(s, 3H), 6.95–7.03(m, 2H), 7.17 (d, 1H), 7.32(d, 1H), 7.44(dd, 1H), 7.58–7.64(m, 2H), 8.04(s, 1H), 8.57(d, 1H), 9.72(d, 1H), 9.84(s, 1H) | 336 |

Example 39

2-[4-(N-Methylsulphamoyl)anilino]-4-(imidazo[1,2a]pyrid-3-yl)pyrimidine

Toluene (4 ml) was added to a mixture of tris(dibenzideneacetone)dipalladium(0) (24 mg, 0.026 mmol), 0.2,2'-bis(diphenylphosphino)-1,1'-binaphthyl (21 mg, 0.034 mmol), 2-chloro-4-(imidazo[1,2a]pyrid-3-yl)pyrimidine (Method 20; 150 mg, 0.652 mmol) and 4-(N-methylsulphamoyl)aniline (Method 23; 135 mg, 0.725 mmol) under nitrogen. The flask was evacuated and refilled with nitrogen and sodium tert-butoxide (140 mg, 1.46 mmol) was added and the flask was re-evacuated and refilled with nitrogen. The mixture was heated at 100° C. for 3 hours and then allowed to cool. The mixture was diluted with ethyl acetate and washed with water. The organic phase was separated, dried and the volatiles removed by evaporation. The residue was purified by chromatography eluting with ethyl acetate/methanol (100:0 increasing in polarity to 97:3) to give the title compound (15 mg, 60% yield). NMR: 2.42 (d, 3H), 7.25–7.10 (m, 2H), 7.52–7.45 (m, 2H), 7.79–7.70 (m, 3H), 7.98 (d, 2H), 8.50 (d, 1H), 8.62 (s, 1H); m/z: 381 [MH]$^+$.

Examples 40–44

Following the procedure of Example 39 and using the appropriate starting materials the following compounds were prepared,

Example 45

2-{4-[N-(3-Hydroxypropyl)sulphamoyl]anilino}-4-(imidazo[1,2a]pyrid-3-yl)pyrimidine 2-Anilino-4-(imidazo[1,2a]pyrid-3-yl)pyrimidine (Example 16; 100 mg, 0.347 mmol) was dissolved in thionyl chloride (4 ml) and the mixture was cooled to 5° C. Chlorosulphonic acid (0.06 ml, 0.90 mmol) was added and the mixture was stirred at 5° C. for 30 minutes, then allowed to warm to ambient temperature and stirred for 60 minutes. The mixture was then heated at reflux for 90 minutes. The volatiles were removed by evaporation and the residue azeotroped with toluene. 3-Aminopropanol (3 ml) was added to the residue and the mixture stirred at ambient temperature for 30 minutes. The mixture was purified chromatography eluting with hexane/ethyl acetate (50:50) increasing in polarity to ethyl acetate/methanol (85:15) (60 mg, 41% yield). NMR: 1.45–1.56 (m, 2H), 2.79 (q, 2H), 3.35 (q, 2H), 4.39 (t, 1H), 7.15 (dd, 1H), 7.31 (t, 1H), 7.45–7.54 (m, 2H), 7.70–7.79 (m, 3H), 7.95 (d, 2H), 8.50 (d, 1H), 8.62 (s, 1H); m/z: 423 [M–H]$^-$.

Examples 46–50

Following the procedure of Example 45 and using the appropriate starting materials the following compounds were prepared,

| Ex | Compound | NMR | m/z [MH]$^+$ | SM |
|---|---|---|---|---|
| 40[1] | 2-{4-[N-(2-Methoxyethyl)sulphamoyl]anilino}-4-(imidazo[1,2a]pyrid-3-yl)pyrimidine | 2.90(q, 2H), 3.18(s, 3H), 3.28–3.30(m, 2H), 7.16(dd, 1H), 7.48–7.54(m, 3H), 7.71–7.80 (m, 3H), 7.95(d, 2H), 8.50(d, 1H), 8.62(s, 1H) | 425 | Meth 24 |
| 41[2] | 2-[4-(N-Propylsulphamoyl)anilino]-4-(imidazo[1,2a]pyrid-3-yl)pyrimidine | 0.80(t, 3H), 1.34–1.42(m, 2H), 2.65–2.75(m, 2H), 7.15(dd, 1H) 7.17(dd, 1H), 7.55–7.48(m, 2H), 7.70–7.79(m, 3H), 7.95(d, 2H), 8.50(d, 1H), 8.63(s, 1H) | 409 | Meth 25 |
| 42 | 2-[4-(N-Cyclopropylsulphamoyl)anilino]-4-(imidazo[1,2a]pyrid-3-yl)pyrimidine | 0.00–0.05(m, 2H), 0.09–0.12(m, 2H), 1.70–1.75(m, 1H), 6.79 (dd, 1H), 7.10–7.15(m, 2H), 7.32–7.42(m, 4H), 7.60(d, 2H), 8.12(d, 1H), 8.28(s, 1H), 9.74 (s, 1H), 9.75(s, 1H) | 405 [M – H]$^-$ | Meth 26 |
| 43 | 2-[4-(N,N-Dimethylcarbamoyl)anilino]-4-(imidazo[1,2a]pyrid-3-yl)pyrimidine | 2.98(s, 6H), 7.10(dd, 1H), 7.3.8–7.50(m, 3H), 7.72–7.82(m, 3H), 8.45(d, 1H), 8.61(s, 1H), 9.82(s, 1H) | 359 | |
| 44[3] | 2-[4-(N-Methylcarbamoyl)anilino]-4-(imidazo[1,2a]pyrid-3-yl)pyrimidine | 2.78(d, 3H), 7.15(dd, 1H), 7.43 (d, 1H), 7.50(dd, 1H), 7.75–7.82 (m, 5H), 8.24(d, 1H), 8.48(d, 1H), 8.62(s, 1H), 9.90(s, 1H) | 345 | |

[1]Product was purified by chromatography eluting with Hexane/ethyl acetate (70:30) increasing in polarity to (0:100).
[2]Product was purified by chromatography eluting with Hexane/ethyl acetate (50:50) increasing in polarity to ethyl acetate/methanol (95:5).
[3]Product was purified by chromatography eluting with Hexane/ethyl acetate (80:20) increasing in polarity to ethyl acetate/methanol (90:10).

| Ex | Compound | NMR | m/z [MH]+ |
|---|---|---|---|
| 46 | 2-{4-[N-(Cyclopropylmethyl)sulphamoyl]anilino}-4-(imidazo[1,2a]pyrid-3-yl)pyrimidine | 0.00–0.04(m, 2H), 0.25–0.32(m, 2H), 0.70–0.78(m, 1H), 2.60(t, 2H), 7.10 (dd, 1H), 7.28–7.42(m, 3H), 7.68–7.75 (m, 3H), 7.87(d, 2H), 8.42(d, 1H), 8.60(s, 1H) | 421 |
| 47 | 2-{4-[N-(5-Hydroxypentyl)sulphamoyl]anilino}-4-(imidazo[1,2a]pyrid-3-yl)pyrimidine | 1.18–1.40(m, 8H), 2.70(t, 2H) 4.25 (br s, 1H), 7.15(dd, 1H), 7.48–7.52(m, 2H), 7.70–7.78(m, 3H), 7.95(d, 2H), 8.50(d, 1H), 8.62(s, 1H) | 453 |
| 48 | 2-(4-{N-[2-(1-Methylpyrrolidin-2-yl)ethyl]sulphamoyl}anilino)-4-(imidazo[1,2a]pyrid-3-yl)pyrimidine | 1.18–1.25(m, 2H), 1.48–1.58(m, 2H), 1.60–1.70(m, 1H), 1.90–2.00(m, 2H), 2.10(s, 3H), 2.70–2.85(m, 4H), 7.15 (dd, 1H), 7.40(s, 1H), 7.48–7.53(m, 2 H), 7.70–7.80(m, 3H), 7.95(d, 2H), 8.50(d, 1H), 8.63(s, 1H) | 476 [M − H]− |
| 49 | 2-{4-[N-(3-Diethylaminopropyl)sulphamoyl]anilino}-4-(imidazo[1,2a]pyrid-3-yl)pyrimidine | 0.86(t, 6H), 1.42(q, 2H), 2.30(q, 4 H), 2.38–2.42(m, 2H), 2.75(q, 2H), 7.15(dd, 1H), 7.42–7.55(m, 2H), 7.70–7.80(m, 3H), 7.95(d, 2H), 8.50 (d, 1H), 8.65(s, 1H) | 480 |
| 50 | 2-{4-[N-(2-Isopropylaminoethyl)sulphamoyl]anilino}-4-(imidazo[1,2a]pyrid-3-yl)pyrimidine | 0.87(s, 3H), 0.90(s, 3H), 2.46–2.50 (m, 2H), 2.58(q, 2H), 2.80(t, 2H), 7.18(dd, 1H), 7.48–7.52(m, 2H), 7.70–7.80(m, 3H), 7.95(d, 2H), 8.50 (d, 1H), 8.62(s, 1H) | 452 |

[1] Product was purified by chromatography eluting with Hexane/ethyl acetate (70:30) increasing in polarity to (0:100).
[2] Product was purified by chromatography eluting with Hexane/ethyl acetate (50:50) increasing in polarity to ethyl acetate/methanol (95:5).
[3] Product was purified by chromatography eluting with Hexane/ethyl acetate (80:20) increasing in polarity to ethyl acetate/methanol (90:10).

Example 51

2-(4-{N-[3-(2-Oxopyrolidin-1-yl)propyl]sulphamoyl}anilino)-4-(imidazo[1,2a]pyrid-3-yl)pyrimidine 2-Anilino-4-(imidazo[1,2a]pyrid-3-yl)pyrimidine (Example 16; 100 mg, 0.347 mmol) was dissolved in thionyl chloride (3 ml) and the mixture was cooled to 5° C. Chlorosulphonic acid (0.06 ml, 0.90 mmol) was added and the mixture was stirred at 5° C. for 30 minutes, allowed to warm to ambient temperature and stirred for 60 minutes. The mixture was then heated at reflux for 90 minutes. The volatiles were removed by evaporation and the residue azeotroped with toluene. Pyridine (3 ml) and 3-(2-oxopyrolidin-1-yl)propylamine (3 ml) were added to the residue and the mixture was stirred at ambient temperature for one hour. The mixture was purified by chromatography eluting with hexane/ethyl acetate (50:50) increasing in polarity to ethyl acetate/methanol (80:20) (60 mg, 36% yield). NMR: 1.51–1.60 (m, 2H), 1.80–1.90 (m, 2H), 2.13 (t, 2H), 2.70 (t, 2H), 3.10 (t, 2H), 3.20 (t, 2H), 7.16 (dd, 1H), 7.48–7.55 (m, 2H), 7.70–7.80 (m, 3H), 7.95 (d, 2H), 8.50 (d, 1H), 8.62 (s, 1H); m/z: 492[MH]+.

Examples 52–70

Following the procedure of Example 45 and using the appropriate starting materials the following compounds were prepared,

| Ex | Compound | NMR | m/z [MH]+ |
|---|---|---|---|
| 52 | 2-{4-[N-(3-Methoxypropyl)sulphamoyl]anilino}-4-(imidazo[1,2a]pyrid-3-yl)pyrimidine | 1.55–1.62(m, 2H), 2.75–2.81(m, 2H), 3.12(s, 3H), 3.23–3.28(m, 2H), 7.15 (dd, 1H), 7.38(t, 1H), 7.55(m, 2H), 7.70–7.80(m, 3H), 7.96(d, 2H), 8.50 (d, 1H), 8.62(s, 1H) | 439 |
| 53 | 2-{4-[N-(3-Isopropylaminopropyl)sulphamoyl]anilino}-4-(imidazo[1,2a]pyrid-3-yl)pyrimidine | 1.48(t, 2H), 1.88(d, 6H), 2.42(t, 2H), 2.59(m, 1H), 2.79(t, 2H), 7.15(dd, 1 H), 7.48–7.55(m, 2H), 7.70–7.80(m, 3 H), 7.95(d, 2H), 8.50(d, 1H), 8.62(s, 1H) | 466 |
| 54 | 2-{4-[N-(3-Imidazol-1-ylpropyl)sulphamoyl]anilino}-4-(imidazo[1,2a]pyrid-3-yl)pyrimidine | 1.80(m, 2H), 2.70(q, 2H), 3.94(t, 2 H), 6.82(s, 1H), 7.08(s, 1H), 7.14(dd, 1H), 7.48–7.52(m, 4H), 7.70(d, 2H), 7.78(d, 1H), 7.98(d, 2H), 8.50(d, 1 H), 8.62(s, 1H) | 473 [M − H]− |
| 55[1] | 2-{4-[N-(3-Dimethylaminopropyl)sulphamoyl]anilino}-4-(imidazo | 1.48(m, 2H), 2.02(s, 6H), 2.12(t, 2 H), 2.78(t, 2H), 7.15(dd, 1H), 7.38(s, | 452 |

-continued

| Ex | Compound | NMR | m/z [MH]+ |
|---|---|---|---|
| | [1,2a]pyrid-3-yl)pyrimidine | 1H), 7.48–7.57(m, 2H), 7.72(d, 2H), 7.78(d, 1H), 7.98(d, 2H), 8.50(d, 1H), 8.62(s, 1H) | |
| 56 | 2-{4-[N-(3-Morpholinopropyl) sulphamoyl]anilino}-4-(imidazo [1,2a]pyrid-3-yl)pyrimidine | 1.52(t, 2H), 2.18–2.22(m, 6H), 2.78 (t, 2H), 3.43–3.48(m, 4H), 7.15(dd, 1H), 7.38(s, 1H), 7.48–7.55(m, 2H), 7.74(d, 2H), 7.78(d, 1H), 7.98(d, 2H), 8.50(d, 1H), 8.62(s, 1H) | 494 |
| 57[1] | 2-{4-[N-(3-Aminopropyl) sulphamoyl]anilino}-4-(imidazo [1,2a]pyrid-3-yl)pyrimidine | 1.38–1.45(m, 4H), 2.79(t, 2H), 7.15 (dd, 1H), 7.48–7.56(m, 2H), 7.60–7.64 (m, 1H), 7.72(d, 2H), 7.79(d, 1H), 7.98(d, 2H), 8.50(d, 1H), 8.62(s, 1H) | 424 |
| 58[1] | 2-(4-{N-[2-(2-Hydroxyethyl amino)ethyl]sulphamoyl}anilino)-4-(imidazo[1,2a]pyrid-3-yl) pyrimidine | 2.75(t, 2H), 2.86–2.90(m, 2H), 3.54 (t, 2H), 3.60(t, 2H), 7.08(d, 2H), 7.18 (dd, 1H), 7.42–7.55(m, 2H), 7.75–7.80 (m, 3H), 8.00(d, 2H), 8.52(d, 1H), 8.62(s, 1H) | 454 |
| 59[2] | 2-{4-[N-(2-Imidazol-4-ylethyl) sulphamoyl]anilino}-4-(imidazo [1,2a]pyrid-3-yl)pyrimidine | 3.10(t, 2H), 3.95(t, 2H), 7.10(d, ⑦H), 7.40(s, 2H), 7.50(d, 2H), 7.58(d, 2H), 7.69(d, 2H), 7.75(d, 1H), 8.45(d, 1H), 8.60(s, 1H), 8.79(s, 1H), 9.75 (s, 1H), 10.1(s, 1H) | |
| 60[1] | 2-{4-[N-(3-Methylaminopropyl) sulphamoyl]anilino}-4-(imidazo [1,2a]pyrid-3-yl)pyrimidine | 1.70–1.78(m, 2H), 2.66(s, 3H), 2.90 (t, 2H), 3.00(t, 2H), 7.08(d, 2H), 7.18 (t, 1H), 7.44(d, 2H), 7.51(m, 1H), 7.70–7.80(m, 3H), 8.02(d, 1H), 8.52 (d, 1H), 8.63(s, 1H) | 436 [M − H]− |
| 61[1] | 2-{4-[N-(2-Piperazin-1-ylethyl) sulphamoyl]anilino}-4-(imidazo [1,2a]pyrid-3-yl)pyrimidine | 2.30(t, 2H), 2.40–2.43(m, 4H), 2.59 (t, 2H), 2.83–2.90(m, 4H), 7.18(dd, 1H), 7.49–7.55(m, 2H), 7.68(d, 2H), 7.78(d, 1H), 8.02(d, 2H), 8.50(d, 1H), 8.62(s, 1H) | |
| 62[1] | 2-(4-{N-[3-(4-Methylpiperazin-1-yl)propyl]sulphamoyl}anilino)-4-(imidazo[1,2a]pyrid-3-yl) pyrimidine | 1.49(m, 2H), 2.10(s, 3H), 2.15–2.25 (m, 8H), 2.78(q, 2H), 3.25–3.29(m, 2H), 7.18(dd, 1H), 7.40(dd, 1H), 7.50 (d, 2H), 7.75(d, 2H), 8.80(d, 1H), 7.95(d, 2H), 8.52(d, 1H), 8.65(s, 1H) | 507 |
| 63[1] | 2-(4-{N-[2-(2-Diethylaminoethyl-amino)ethyl]sulphamoyl}anilino)-4-(imidazo[1,2a]pyrid-3-yl) pyrimidine | 0.93(t, 6H), 2.40–2.58(m, 4H), 2.62 (t, 2H), 2.84(t, 2H), 3.20–3.40(m, 4H), 7.10(d, 1H), 7.18(dd, 1H), 7.42–7.50(m, 3H), 7.72–7.80(m, 3H), 7.98(d, 2H), 8.50(d, 1H), 8.62(s, 1H) | 509 |
| 64[1] | 2-{4-[N-(2,3-Dihydroxypropyl) sulphamoyl]anilino}-4-(imidazo [1,2a]pyrid-3-yl)pyrimidine | 2.66(m, 1H), 2.86(m, 1H), 3.21–3.30 (m, 2H), 3.46(m, 1H), 4.49(t, 1H), 4.70(d, 1H), 7.18(dd, 1H), 7.24(dd, 1H), 7.48–7.52(m, 2H), 7.70–7.80(m, 3H), 7.98(d, 2H), 8.50(d, 1H), 8.62(s, 1H) | 441 |
| 65 | 2-{4-[N-(2-Dimethylaminoethyl) sulphamoyl]anilino}-4-(imidazo [1,2a]pyrid-3-yl)pyrimidine | 2.08(s, 6H), 2.24(t, 2H), 2.82(t, 2H), 1.7(dd, 1H), 7.30(s, 1H), 7.44–7.54 (m, 2H), 7.70–7.80(m, 3H), 7.95(d, 2H), 8.50(d, 1H), 8.63(s, 1H) | 438 |
| 66 | 2-{4-[N-(2-Morpholinoethyl) sulphamoyl]anilino}-4-(imidazo [1,2a]pyrid-3-yl)pyrimidine | 2.34–2.45(m, 6H), 2.87–2.95(m, 2H), 3.46–3.60(m, 4H), 7.09(d, 2H), 7.18 (dd, 1H), 7.42–7.50(m, 3H), 7.74–7.80 (m, 2H), 7.98(d, 2H), 8.50(d, 1H), 8.62(s, 1H) | 478 [M − H]− |
| 67 | 2-{4-[N-(2-Pyrrolidin-1-ylethyl) sulphamoyl]anilino}-4-(imidazo [1,2a]pyrid-3-yl)pyrimidine | 1.64–1.74(m, 4H), 2.52–2.64(m, 6H), 2.87–2.92(m, 2H), 7.18(dd, 1H), 7.44–7.54(m, 3H), 7.72–7.80(m, 3H), 7.98(d, 2H), 8.50(d, 1H), 8.62(s, 1H) | 464 |
| 68 | 2-{4-[N-(2-Methylaminoethyl) sulphamoyl]anilino}-4-(imidazo [1,2a]pyrid-3-yl)pyrimidine | 2.61–2.64(m, 2H), 2.68(s, 3H), 2.90 (t, 2H), 7.18(dd, 1H), 7.48–7.58(m, 2H), 7.68–7.78(m, 4H), 7.95(d, 1H), 8.00(d, 1H), 8.51(d, 2H), 8.64(s, 1H) | 424 |
| 69 | 2-{4-[N-(2-Piperidin-1-ylethyl) sulphamoyl]anilino}-4-(imidazo [1,2a]pyrid-3-yl)pyrimidine | 1.28–1.40(m, 2H), 1.40–1.58(m, 4H), 2.20–2.50(m, 6H), 2.84–2.92(m, 2H), 7.18(dd, 1H), 7.48–7.53(d, 2H), 7.72–7.80(m, 3H), 7.98(d, 2H), 8.50 (d, 1H), 8.62(s, 1H) | 478 |

-continued

| Ex | Compound | NMR | m/z [MH]⁺ |
|---|---|---|---|
| 70 | 2-{4-[N-(2-Diethylaminoethyl) sulphamoyl]anilino}-4-(imidazo [1,2a]pyrid-3-yl)pyrimidine | 0.86(t, 6H), 2.32–2.42(m, 6H), 2.79 (t, 2H), 7.18(dd, 1H), 7.23(s, 1H), 7.48–7.52(m, 2H), 7.70–7.80(m, 3H), 7.98(d, 2H), 8.50(d, 1H), 8.62(s, 1H) | 466 |

[1]Product was purified by chromatography eluting with ethyl acetate/methanol (100:0) increasing in polarity to (70:30).
[2]Product was isolated without chromatography by trituration from reaction mixture with dichloromethane and methanol.

Example 71

2-{4-[N-(3-Imidazol-1-ylpropyl)carbamoyl]anilino}-4-(imidazo[1,2a]pyrid-3-yl)pyrimidine Toluene (10 ml) was added to 2-amino-4-(imidazo[1,2a]pyrid-3-yl)pyrimidine (Method 22; 200 mg, 0.95 mmol), 1-[3-(4-bromobenzoylamino)propyl]imidazole (Method 27; 350 mg, 1.14 mmol), tris(dibenzideneacetone)dipalladium (0) (43 mg, 0.047 mmol) and 2,2'-bis(diphenylphosphino)-1,1'-binaphthyl (28 mg, 0.046 mmol) under nitrogen. Sodium tert-butoxide (218 mg, 0.0023 mmol) was added, the reaction mixture was flushed thoroughly with nitrogen and then heated at 100° C. for 24 hours. The volatiles were removed by evaporation and the residue was purified by chromatography eluting with hexane/ethyl acetate (50:50) increasing in polarity to ethyl acetate/methanol (95:5) to give the title compound (99 mg, 24% yield). NMR: 1.90–2.00 (m, 2H), 3.22 (q, 2H), 4.02 (t, 2H), 6.86 (s, 1H), 7.16 (dd, 1H), 7.21 (s, 1H), 7.42–7.55 (m, 2H), 6.80 (s, 3H), 7.78 (d, 1H), 7.83 (s, 4H), 8.38 (t, 1H), 8.48 (d, 1H), 8.62 (s, 1H), 9.92 (s, 1H); m/z: 439 [MH]⁺.

Examples 72–74

Following the procedure of Example 71 and using the appropriate starting materials the following compounds were prepared,

| Ex | Compound | NMR | m/z [MH]⁺ | SM |
|---|---|---|---|---|
| 72[1] | 2-(4-{N-[3-(2-Oxopyrolidin-1-yl)propyl]carbamoyl} anilino)-4-(imidazo[1,2a]pyrid-3-yl)pyrimidine | 1.70(quin, 2H), 1.90(quin, 2H), 2.21(t, 2H), 3.18–3.24(m, 4H), 3.30–3.38(m, 2H), 7.15(dd, 1H), 7.42–7.52(m, 2H), 7.78(d, 1H), 7.82(s, 4H), 8.27(t, 1H), 8.49(d, 1H), 8.62(s, 1H), 9.90(s, 1H) | 456 | Meth 28 |
| 73[2] | 2-{3-Chloro-4-[N-(2-methoxyethyl)sulphamoyl] anilino}-4-(imidazo[1,2a] pyrid-3-yl)pyrimidine | 3.00(q, 2H), 3.12(s, 3H), 3.25–3.30(m, 2H), 7.18(dd, 1H), 7.50–7.58(m, 2H), 7.68(t, 1H), 7.75–7.80(m, 2H), 7.87(s, 1H), 8.22(s, 1H), 8.55(d, 1H), 8.64(s, 1H) | 459 | |
| 74[3] | 2-[3-Chloro-4-(N-propyl sulphamoyl)anilino]-4-(imidazo[1,2a]pyrid-3-yl) pyrimidine | 0.80(t, 3H), 1.38(m, 2H), 2.79 (q, 2H), 7.18(dd, 1H), 7.48–7.55 (m, 2H), 7.66(dd, 1H), 7.78(dd 2, H), 7.92(d, 1H), 8.25(s, 1H), 8.55(d, 1H), 8.68(s, 1H), 10.10 (d, 1H), 10.26(s, 1H) | 443 | |

[1]Reaction Heated at 100° C. for 48 Hours and purified by chromatography eluting with dichloromethane/methanol (90:10).
[2]Starting from 2,4-dichloro-1-(2-methoxyethylsulphamoyl)benzene (Method 29).
[3]Starting from 2,4-dichloro-1-(1-propylsulphamoyl)benzene (Method 30).

Example 75

2-(3-Methyl-4-sulphamoylanilino)-4-(imidazo[1,2a]pyrid-3-yl)pyrimidine 2-(3-Methylanilino)-4-(imidazo[1,2a]pyrid-3-yl)pyrimidine (Example 35; 80 mg, 0.266 mmol) was treated as described in Example 45 but with 2 M ethanolic ammonia to give the title compound (6 mg, 17% yield). NMR: 2.60 (s, 3H), 6.95–7.20 (m, 4H), 7.46–7.50 (m, 2H), 7.70–7.80 (m, 4H), 8.50 (d, 1H), 8.62 (s, 1H), 9.87 (s, 1H); m/z: 381 [MH]$^+$.

7.84 (d, 2H), 8.76 (s, 1H), 8.78 (s, 1H), 9.62 (s, 1H); m/z: 445 [MH]$^+$.

Examples 76–78

Following the procedure of Example 75 and using the appropriate starting materials the following compounds were prepared, Examples 80–81

Following the procedure of Example 79 and using the appropriate starting materials the following compounds were prepared,

| Ex | Compound | NMR | m/z [MH]$^+$ |
|---|---|---|---|
| 76 | 2-{3-Methyl-4-[N-(2-methoxy-ethyl)sulphamoyl]anilino}-4-(imidazo[1,2a]pyrid-3-yl)pyrimidine | 2.55(s, 3H), 2.91(q, 2H), 3.11(s, 3H), 3.22(t, 2H), 7.12(dd, 1H), 7.44–7.55(m, 3H), 7.74–7.80(m, 4H), 8.50(d, 1H), 8.62(s, 1H), 9.98(s, 1H) | 439 |
| 77 | 2-{3-Methyl-4-[N-(3-morpholino-propyl)sulphamoyl]anilino}-4-(imidazo[1,2a]pyrid-3-yl)pyrimidine | 1.49(m, 2H), 2.13–2.20(m, 4H), 3.24–3.32(m, 2H), 2.58(s, 3H), 2.80(t, 2H), 3.42–3.48(m, 4H), 7.12(dd, 1H), 7.48–7.53(m, 2H), 7.75–7.80(m, 4H), 8.50(d, 1H), 8.62(s, 1H) | 508 |
| 78 | 2-{3-Methyl-4-[N-(2-morpholino-ethyl)sulphamoyl]anilino}-4-(imidazo[1,2a]pyrid-3-yl)pyrimidine | 2.18–2.21(m, 4H), 2.30–3.38(m, 2H), 2.59(s, 3H), 2.87(t, 2H), 3.42–3.48(m, 4H), 7.12(dd, 1H), 7.42–7.55(m, 3H), 7.75–7.80(m, 4H), 8.50(d, 1H), 8.62(s, 1H), 9.98(s, 1H) | 494 |

Example 79

5-Bromo-2-(4-sulphamoylanilino)-4-(imidazo[1,2a]pyrid-3-yl)pyrimidine

2-Anilino-5-bromo-4-(imidazo[1,2a]pyrid-3-yl)pyrimidine (Example 97; 73 mg, 0.2 mmol) was treated as described in Example 45 but with 2 M ethanolic ammonia to give the title compound (18 mg, 21% yield). NMR: 7.12 (dd, 1H), 7.19 (s, 2H), 7.53 (dd, 2H), 7.72 (d, 2H), 7.79 (d, 1H),

| Ex | Compound | NMR | m/z [MH]$^+$ |
|---|---|---|---|
| 80 | 5-Bromo-2-{4-[N-(2-methoxy-ethyl)sulphamoyl]anilino}-4-(imidazo[1,2a]pyrid-3-yl)pyrimidine | 2.90(m, 2H), 3.18(s, 3H), 3.28(q, 2H), 7.10(dd, 1H), 7.48–7.58(m, 2H), 7.70(d, 2H), 7.79(d, 1H), 7.86(d, 2H), 8.76(s, 1H), 8.78(s, 1H), 9.60(d, 1H) | 503 |
| 81 | 5-Bromo-2-{4-[N-(2-dimethyl-aminoethyl)sulphamoyl]anilino}-4-(imidazo[1,2a]pyrid-3-yl)pyrimidine | 2.06(s, 6 H), 2.25(t, 2H), 2.82(t, 2H), 7.15(dd, 1H), 7.30(s, 1H), 7.55(dd, 1H), 7.72(d, 2H), 7.80(d,1H), 7.90(d, 2H), 8.75(s, 1H), 9.80(s, 1H), 9.65(d, 1H), 10.28(s, 1H) | 516 |
| 82[1] | 5-Bromo-2-{4-[N-(3-dimethyl-aminopropyl)sulphamoyl]anilino}-4-(imidazo[1,2a]pyrid-3-yl)pyrimidine | 1.70–1.80(m, 2H), 1.87–1.98(m, 2H), 2.62(d, 6 H), 2.79(q, 2H), 7.12(dd, 1H), 7.55(dd, 1H), 7.59(dd, 1H), 7.70(d, 2H), 7.79(d, 1H), 7.90(d, 2H), 8.78(s, 1H), 8.79(s, 1H), 9.64(d, 1H), 10.32(s, 1H) | 530 |

[1] Product was purified by chromatography eluting with hexane/ethyl acetate (50:50) increasing in polarity to ethyl acetate/methanol (70:30).

Example 83

2-{4-[N-(2-Methoxyethyl)sulphamoyl]anilino}-4-(5-bromoimidazo[1,2a]pyrid-3-yl)pyrimidine 2-Anilino-4-(5-bromoimidazo[1,2a]pyrid-3-yl)pyrimidine (Example 98; 70 mg, 0.2 mmol) was treated with 2-methoxyethylamine under the conditions described in Example 51 to give the title compound (23 mg, 25% yield). NMR: 2.90 (q, 2H), 3.18 (s, 3H), 3.26–3.29 (m, 2H), 7.49–7.54 (m, 2H), 7.60 (dd, 1H), 7.74–7.78 (m, 3H), 7.90 (d, 1H), 8.54 (d, 1H), 8.62 (s, 1H); m/z: 503 [MH]$^+$.

Example 84

2-{4-[N-(2-Methoxyethyl)sulphamoyl]anilino}-4-(5-phenylthioimidazo[1,2a]pyrid-3-yl)pyrimidine Sodium hydride (80 mg of a 60% suspension in mineral oil, 2.0 mmol) was added to thiophenol (0.102 ml, 1.0 mmol) in NMP (4 ml) and the mixture was stirred for 30 minutes.

2-[4-(N-(2-Methoxyethyl)sulphamoyl)anilino]-4-(5-bromoimidazo[1,2a]pyrid-3-yl)pyrimidine (Example 83; 100 mg, 0.19 mmol) in NMP (1 ml) was added and the mixture was heated at 150° C. for 18 hours. The mixture was allowed to cool, diluted with water and extracted with ethyl acetate. The extracts were washed with water, dried and the volatiles removed by evaporation. The residue was triturated with diethylene ether and collected by filtration to give the title compound (20 mg, 20% yield). NMR: 2;85 (q, 2H), 3.15 (s, 3H), 3.24 (q, 2H), 7.10–7.30 (m, 5H), 7.38 (d, 1H), 7;46 (dd, 1H), 7.52 (d, 1H), 7.75 (d, 2H), 7.79 (d, 1H), 7.92 (d, 2H), 8.54 (d, 1H), 8.66 (s, 1H); m/z: 533 [MH]$^+$.

Examples 85–88

Following the procedure of Example 84 and using the appropriate starting materials the following compounds were prepared,

| Ex | COMPOUND | NMR | m/z [MH]$^+$ |
|---|---|---|---|
| 85[1] | 2-{4-[N-(2-Methoxyethyl)sulphamoyl]anilino}-4-(5-ethylthioimidazo[1,2a]pyrid-3-yl)pyrimidine | 1.18(t, 3H), 2.84–2.95(m, 4H), 3.18 (s, 3H), 3.26–3.30(m, 2H), 7.49–7.58 (m, 3H), 7.71–7.79(m, 4H), 7.90(d, 2H), 8.50–8.55(m, 1H), 8.60(s, 1H), 8.89(s, 1H) | 485 |
| 86[1] | 2-{4-[N-(2-Methoxyethyl)sulphamoyl]anilino}-4-[5-(2-hydroxyethylthio)imidazo[1,2a]pyrid-3-yl]pyrimidine | 2.90(t, 2H), 3.05(t, 2H), 3.20(s, 3H), 3.32(t, 2H), 3.60(q, 2H), 5.00(t, 1H), 7.45(dd, 1H), 7.50(d, 1H), 7.58(d, 1H), 7.70–7.79(m, 3H), 7.95(d, 2H), 8.50(d, 1H), 8.59(s, 1H), 9.95(s, 1H), 10.05(s, 1H) | 501 |
| 87[2] | 2-{4-[N-(2-Methoxyethyl)sulphamoyl]anilino}-4-[5-(thien-2-ylthio)imidazo[1,2a]pyrid-3-yl]pyrimidine | 2.90(m, 2H) 3.15(s, 3H), 3.24(q, 2H), 7.08-7.10(m, 1H), 7.32(d, 1H), 7.42(d, 1H), 7.50(d, 1H), 7.70–7.80 (m, 4H), 7.94(d, 2H), 8.52(d, 1H), 8.63(s, 1H) | 539 |
| 88[3] | 2-{4-[N-(2-Methoxyethyl)sulphamoyl]anilino}-4-[5-(2-dimethylaminoethylthio)imidazo[1,2a]pyrid-3-yl]pyrimidine | 2.15(s, 6H), 2.40–2.50(m, 2H), 2.90 (q, 2H), 3.09(t, 2H), 3.20(s, 3H), 3.28–3.32(m, 2H), 7.48–7.58(m, 3H), 7.72–7.80(m, 3H), 7.95(d, 2H), 8.51 (d, 1H), 8.60(s, 1H), 9.90(s, 1H), 10.11(s, 1H) | 528 |

[1]Product was purified by chromatography eluting with ethyl acetate/methanol (100:0) increasing in polarity to (95:5).
[2]Product was purified by chromatography eluting with ethyl acetate.
[3]Product was purified by chromatography eluting with ethyl acetate/methanol (100:0) increasing in polarity to (70:30).

Example 89

2-{4-[N-(2-Methoxyethyl)sulphamoyl]anilino}-4-(5-cyanoimidazo[1,2a]pyrid-3-yl)pyrimidine 2-{4-[N-(2-Methoxyethyl)sulphamoyl]anilino}-4-(5-bromoimidazo[1,2a]pyrid-3-yl)pyrimidine (Example 83; 87 mg, 0.17 mmol), tetraethylammonium cyanide (27 mg, 0.17 mmol), diphenylphosphinoferrocene (23 mg, 0.03 mmol) copper (1) cyanide (62 mg, 0.7 mmol) and tris(dibenzideneacetone)dipalladium(0) (7 mg, 0.008 mmol) in dry dioxane (6 ml) was flushed thoroughly with nitrogen and heated at reflux for 48 hours. The volatiles were removed by evaporation and the residue was purified by chromatography eluting with hexane/ethyl acetate (50:50) increasing in polarity to (0:100) to give the title compound (16 mg, 21% yield). NMR: 2.90 (q, 2H), 3.15 (s, 3H), 3.25–3.30 (m, 2H), 7.42 (dd, 1H), 7.58 (d, 1H), 7.72–7.78 (m, 3H), 7.90 7.98 (m, 3H), 8.59 (d, 1H), 8.40 (s, 1H), 10.23 (s, 1H), 10.53 (s, 1H); m/z: 447 [M–H]$^-$.

Example 90

2-{4-[N-(3-Dimethylaminopropyl)sulphamoyl]anilino}-4-(5-bromoimidazo[1,2a]pyrid-3-yl)pyrimidine 2-Anilino-4-(5-bromoimidazo[1,2a]pyrimidine (Example 98; 200 mg, 0.52 mmol) was prepared as described in Example 45 but treated with 3-dimethylaminopropylamine to give the title compound (92 mg, 34% yield). NMR: 1.48–1.58 (m, 2H), 2.10 (s, 6H), 2.20–2.28 (m, 2H), 2.72–2.80 (m, 2H), 7.08 (d, 1H), 7.40–7.48 (m, 2H), 7.51 (d, 1H), 7.61 (dd, 1H), 7.71–7.78 (m, 3H), 7.90 (d, 2H), 8.55 (d, 1H), 8.64 (s, 1H); m/z: 530 [MH]$^+$.

Example 91

5-(2-Hydroxyethylthio)-2-{4-[N-(2-Methoxyethyl)sulphamoyl]anilino)}-4-(imidazo[1,2a]pyrid-3-yl)pyrimidine Sodium hydride (158 mg of a 60% suspension in mineral oil, 4.0 mmol) was added to 2-mercaptoethanol (0.139 ml, 2.0 mmol) in NMP (4 ml) and the mixture was stirred for 30 minutes.
5-Bromo-2-{4-[N-(2-methoxyethyl)sulphamoyl]anilino}-4-(imidazo[1,2a]pyrid-3-yl)pyrimidine (Example 80; 100 mg, 0.19 mmol) in NMP (1 ml) was added and the mixture was heated at 120° C. for 3 hours. The mixture was allowed to cool, diluted with water, neutralised with 2 M hydrochloric acid and extracted with ethyl acetate. The extracts were washed with water and brine, dried and the volatiles removed by evaporation. The residue was purified by chromatography eluting with hexane/ethyl acetate (50:50) increasing in polarity to ethyl acetate/methanol (95:5) to give the title compound (39 mg, 20% yield). NMR: 2.85–2.98 (m, 4H), 3.15 (s, 3H), 3.24–3.30 (m, 2H), 3.51 (q, 2H), 4.82 (t, 1H), 7.10 (dd, 1H), 7.45–7.54 (in, 2H), 7.70 (d, 2H), 7.78 (d, 1H), 7.90 (d, 2H), 8.70 (s, 1H), 8.85 (s, 1H), 9.72 (d, 1H), 10.18 (s, 1H); m/z: 501 [MH]$^+$.

Example 92

2-(4-{N-[3-(tert-Butoxycarbonylamino)propyl]sulphamoyl}anilino)-4-(imidazo[1,2a]pyrid-3-ylpyrimidine 2-Anilino-4-(imidazo[1,2a]pyrid-3-yl)pyrimidine (Example 16; 290 mg, 1.0 mmol) was dissolved in thionyl chloride (6 ml) and the mixture was cooled to 0° C. Chlorosulphonic acid (0.266 ml, 4.0 mmol) was added slowly and the mixture was stirred at 0° C. for 30 minutes, allowed to warm to ambient temperature stirred for two hours and then heated at reflux for one hour. The volatiles were removed by evaporation. The residue was dissolved in dry pyridine (5 ml) and the resulting solution added slowly to a solution of 3-(tert-butoxycarbonylamino)propylamine (0.209 ml, 1.2 mmol) and diethylmethylamine (1.21 ml, 10 mmol) in pyridine (10 ml) and cooled to 0° C. under nitrogen. The mixture was stirred at 0° C. for one hour, then at ambient temperature for two hours. The volatiles were removed by evaporation and the residue azeotroped with water. The residue was triturated with water, collected by filtration, and then purified by chromatography eluting with dichloromethane/methanol (95:5) increasing in polarity to (90:10) to give the title compound (207 mg, 40% yield). NMR: 1.30 (s, 9H), 1.50 (quin, 2H), 2.67 (m, 2H), 2.85 (m, 2H), 7.38 (m, 2H), 7.58 (d, 1H), 7.68 (d, 1H), 7.70 (d, 2H), 7.89 (d, 1H), 7.95 (d, 2H), 8.58 (d, 1H), 8.80 (s, 1H); m/z: 524 [MH]$^+$.

Example 93

2-(4-{N-[3-(Benzyloxycarbonylamino)propyl]sulphamoyl}anilino)-4-(imidazo[1,2a]pyrid-3-yl)pyrimidine 2-Anilino-4-(imidazo[1,2a]pyrid-3-yl)pyrimidine (Example 16; 290 mg, 1.0 phenol) and 3-(benzyloxycabonylamino)propylamine (0.294 ml, 1.2 mmol) were treated as described in Example 92 to give the title compound (212 mg, 38% yield). NMR: 1.50 (quin, 2H), 2.70 (q, 2H), 2.98 (dd, 2H), 4.98 (s, 2H), 7.12–7.15 (m, 4H), 7.18 (t, 2H), 7.19 (t, 1H), 7.75 (d, 2H), 7.79 (d, 1H), 7.90 (d, 2H), 8.50 (d, 1H), 8.60 (s, 1H); m/z: 558 [MH]$^+$.

Example 94

2-[4-(2-Diethylaminoethoxy)anilino]-4-(6-phenylimidazo[1,2a]pyrid-3-yl)pyrimidine 3-(3-Dimethylaminoprop-2-en-1-oyl)-6-phenylimidazo[1,2a]pyridine (Method 38; 50 mg, 0.17 mmol) was added to a solution of 4-(2-diethylaminoethoxy)phenylguanidine (Method 42; 60 mg, 0.19 mmol) and sodium methoxide (11 mg, 0.21 mmol) in n-butanol (1.5 ml) and the mixture was heated at 115° C. for 15 hours. The volatiles were removed by evaporation and the residue purified by chromatography eluting with hexanelethyl acetate (50:50) increasing in polarity to ethyl acetate/methanol (80:20) to give the title compound (5 mg, 6% yield). NMR: 1.07 (t, 6H), 2.64 (q, 4H), 2.92 (t, 2H), 4.10 (t, 2H), 6.98 (d, 2H), 7.08 (m, 2H), 7.15 (d, 1H), 7.37–7.60 (m, 4H), 7.70 (d, 2H), 7.92 (s, 1H), 8.30 (s, 1H), 8.35 (d, 1H), 9.80 (d, 1H); m/z: 479 [MH]$^+$.

Example 95

4-(6-Methoxy-2-methylimidazo[1,2a]pyrid-3-yl)-2-(4-sulphamoylanilino)pyrimidine 3-(3-Dimethylaminoprop-2-en-1-oyl)-2-methyl-6-methoxyimidazo[1,2a]pyridine (Method 39; 862 mg, 3.51 mmol) was added to a solution of 4-sulphamoylphenylguanidine (Method 41; 1.5 g, 7.0 mmol) and sodium methoxide (758 mg, 14 mmol) in N-butanol (4 ml) and the mixture was heated at reflux for 24 hours. The mixture was allowed to cool and the resulting precipitate collected by filtration and purified by chromatography eluting with hexane/ethyl acetate (50:50) increasing in polarity to ethyl acetate/methanol (90:10) to give the title compound. NMR: 2.60 (s, 3H), 3.88 (s, 3H), 6.70 (dd, 1H), 7.03 (d, 1H), 7.12 (d, 1H), 7.18 (s, 2H), 7.75 (d, 2H), 7.90 (d, 2H), 8.52 (d, 1H), 9.68 (d, 1H), 9.97 (s, 1H); m/z: 411 [MH]$^+$.

Example 96

2-(3-Chloroanilino)-4-(pyrazolo[2,3a]pyrid-3-yl)pyrimidine

Dry n-butanol (6.0 ml) was added to a mixture of 3-(3-dimethylaminoprop-2-en-1-oyl)-2-methylpyrazolo[2,3a]pyridine (Method 18; 180 mg, 0.84 mmol), 3-chlorophenylguanidine (142 mg, 0.84 mmol) and sodium hydride (67 mg of a 60% dispersion in mineral oil, 1.67 mmol) and the mixture was heated under nitrogen at 125° C. for 7 hours. The volatiles were removed by evaporation and the residue was triturated with a mixture of diethylene ether and distilled water. The precipitated solid was collected by filtration, washed with diethylene ether and distilled water and dried to give the title compound (78 mg, 29% yield). NMR: 7.00 (d, 1H), 7.10 (t, 1H), 7.35 (m, 2H), 7.50 (t, 1H), 7.60 (d, 2H), 8.08 (s, 1H), 8.43 (d, 1H), 8.70 (d, 1H), 8.82 (d, 2H), 9.68 (s, 1H); m/z: 322 [MH]+.

Example 97

2-Anilino-5-bromo-4-(imidazo[1,2a]pyrid-3-yl)pyrimidine

2-Amino-5-bromo-4-(imidazo[1,2a]pyrid-3-yl)pyrimidine (Method 31; 200 mg, 0.67 mmol) and bromobenzene (0.08 ml, 0.76 mmol) were treated as described in Example 71 and the product was purified by chromatography eluting with hexane/ethyl acetate (50.50) increasing in polarity to (0:100) to give the title compound. NMR: 6.98–7.10 (m, 2H), 7.30 (dd, 2H), 7.50 (dd, 1H), 7.66 (d, 2H), 7.78 (d, 1H), 8.64 (s, 2H), 8.72 (s, 1H), 9.01 (d, 1H), 9.82 (s, 1H).

Example 98

2-Anilino-4-(5-bromoimidazo[1,2a]pyrid-3-yl)pyrimidine

2-Amino(5-bromoimidazo[1,2a]pyrid-3-yl)pyrimidine (Method 35; 1.0 g, 3.4 mmol), and bromobenzene (4.36 ml, 4.1 mmol) were treated as described in Example 71 and the product purified by chromatography eluting with ethyl acetate/methanol (98:2) increasing in polarity to (90:10) to give the title compound (70 mg; 6% yield) NMR: 7.00 (dd, 1H), 7.30–7.40 (m, 4H), 7.59 (d, 1H), 7.65–7.75 (m, 3H), 8.42 (d, 1H), 8.60 (s, 1H), 9.70 (s, 1H); m/z: 364 [M–H]−.

Example 99

2-(4-Morpholinoanilino)-4-(imidazo[1,2a]pyrid-3-yl)pyrimidine

To a solution of 4-morpholinoaniline (192 mg, 1.08 mmol) in N,N-dimethylformamide (2 ml) was added sodium hydride (54 mg of a 60% suspension in mineral oil, 1.35 mmol), and the resulting brownish suspension was allowed to stir for ten minutes at room temperature. To this mixture was added 4-(imidazo[1,2a]pyrid-3-yl)-2-ethylthiopyrimidine (131 mg, 0.539 mmol), and the reaction mixture was heated at 130° C. for 3 h. The solvent was removed in vacuo, and the residue was suspended in water. The obtained solid was filtered off and washed with water, several portions of diethyl ether, and ethyl acetate to afford 46 mg (22% yield) of the title compound as a brownish solid: mp (decomp) >250° C.; $^1$H NMR (400 MHz, DMSO-d$_6$) δ 10.06 (broad s, 1H), 9.44 (s, 1H), 8.60 (s, 1H), 8.38 (d, J=5.3 Hz, 1H), 7.77 (d, J=9.0 Hz, 1H), 7.56 (d, J=8.5 Hz, 2H), 7.51–7.46 (m, 1H), 7.33 (d, J=5.4 Hz, 1H), 7.11–7.02 (m, 1H), 6.97 (d, J=8.9 Hz, 2H), 3.78–3.74 (m, 4H), 3.10–3.06 (m, 4H); $^{13}$C NMR (400 MHz, DMSO-d$_6$)) δ 160.9, 158.1, 157.8, 148.9, 148.5, 138.3, 132.2, 129.7, 126.9, 123.8, 122.2, 118.2, 116.8, 113.7, 107.4, 67.4, 50.4; MS (EI) m/z (relative intensity) 372 (100, M+), 313 (30).

Example 100

2-(4-Ethoxyanilino)-4-(imidazo[1,2a]pyrid-3-yl)pyrimidine

The title compound was prepared from 4-(imidazo[1,2a]pyrid-3-yl)-2-methylthiopyrimidine and 4-ethoxyaniline following the general method of Example 1 affording 20 mg (15% yield) of the title compound as a solid: $^1$H NMR (400 MHz, DMSO-d$_6$)) δ 10.07 (broad s, 1H), 9.48 (s, 1H), 8.60 (s, 1H), 8.39 (d, J=5.3 Hz, 1H), 7.77 (d, J=8.9 Hz, 1H), 7.59 (d, J=8.8 Hz, 2H), 7.52–7.46 (m, 1H), 7.34 (d, J=5.3 Hz, 11H), 7.12–7.08 (m, 1H), 6.93 (d, J=9.0 Hz, 2H), 4.02 (q,J=7.0 Hz, 2H), 1.34 (t, J=6.9 Hz, 3H); MS (ESP) m/z 332 (M+1).

Example 101

2-(3,5-Dimethoxyanilino)-4-(imidazo[1,2a]pyrid-3-yl)pyrimidine

The title compound was prepared from 4-(imidazo[1,2a]pyrid-3-yl)-2-methylthiopyrimidine and 3,5-dimethoxyaniline following the general method of Example 1. An additional purification of the product was performed by column chromatography on silica gel using chloroform/ethanol, 98:2, as the eluent affording 9 mg(6% yield) of the title compound as a greyish solid: $^1$H NMR (400 MHz, CDCl$_3$) δ 9.93 (d, J=7.0 Hz, 1H), 8.39 (d, J=5.3 Hz, 1H), 8.30 (s, 1H), 7.73 (d, J=9.0 Hz, 1H), 7.39–7.34 (m, 1H), 7.18 (s, 1H), 7.12 (d, J=5.4 Hz, 1H), 6.97–6.92 (m, 1H), 6.84 (app d, J=2.1 Hz, 2H), 6.27 (app t, J=2.2 Hz, 1H), 3.81 (s, 6H); MS (TSP) m/z 348 (M+1).

Example 102

2-(4-Fluoro-3-methylanilino)-4-(imidazo[1,2a]pyrid-3-yl)pyrimidine

The title compound was prepared from 4-(imidazo[1,2a]pyrid-3-yl)-2-methylthiopyrimidine and 4-fluoro-3-methylaniline following the general method of Example 1. An additional purification of the product was performed by column chromatography on silica gel using chloroform/ethanol, 98:2, as the eluent affording 21 mg (12% yield) of the title compound as a pale yellow, solid: $^1$H NMR (400 MHz, CDCl$_3$) δ 9.79 (d, J=7.0 Hz, 1H), 8.36 (d, J=5.4 Hz, 1H), 8.30 (s, 1H), 7.72 (d, J=9.0 Hz, 1H), 7.44 (dd, J=6.7, J=2.6 Hz, 1H), 7.38–7.26 (m, 3H), 7.10 (d, J=5.4 Hz, 1H), 7.03 (app t, J=8.9 Hz, 1H), 6.89–6.85 (m, 1H), 2.32 (s, 3H); $^{13}$C NMR (CDCl$_3$) δ 160.2, 157.8 (d, J$_F$=242 Hz), 157.6, 157.4, 148.6, 138.0, 134.8 (d, J$_F$=2.8 Hz), 129.1, 126.6, 125.3 (d, J$_F$=18 Hz), 124.7 (d, J$_F$=4.7 Hz), 121.7, 120.6 (d, J$_F$=7.8 Hz), 117.8, 115.1 (d, J$_F$=23 Hz), 113.4, 107.3, 14.8 (d, J$_F$=3.3 Hz); MS (TSP) m/z 320 (M+1).

Example 103

2-(4-Cyanoanilino)-4-(imidazo[1,2a]pyrid-3-yl)pyrimidine

The title compound was prepared from 4-(imidazo[1,2a]pyrid-3-yl)-2-methylthiopyrimidine and 4-aminobenzonitrile following the general method of Example 1 affording 120 mg (85% yield) of the title compound as an off-white solid: mp>300° C.; $^1$H NMR (400 MHz, DMSO-d$_6$)) δ 10.24 (s, 1H), 10.12 (d, J=7.0 Hz, 1H), 8.68 (s, 1H), 8.54 (d, J=5.5

Hz, 1H, 8.01 (d, J=8.7 Hz, 2H), 7.82–7.77 (m, 3H), 7.57–7.52 (m, 2H), 7.25–7.20 (m, 1H); MS (TSP) m/z 313 (M+1).

Example 104

2-(4-Carbamoylanilino)-4-(imidazo[1,2a]pyrid-3-yl) pyrimidine

A solution of 2-(4-cyanoanilino)-4-(imidazo[1,2a]pyrid-3-yl)pyrimidine (34 mg, 0.109 mmol) in conc. sulfuric acid (0.5 ml) was stirred at room temperature for 2.5 days. The mixture was cooled on ice, and water was added followed by dropwise addition of 45% NaOH solution. The resulting solid was filtered off and washed with water and diethyl ether. The collected solid was air-dried affording 30 mg (83% yield) of the title compound as a brown-white solid: mp>300° C.; $^1$H NMR (400 MHz, DMSO-d$_6$)) δ 10.15 (d, J=6.9 Hz, 1H), 9.97 (s, 1H), 8.66 (s, 1H), 8.51 (d, J=5.4 Hz, 1H), 7.90–7.78 (m, 6H), 7.55–7.50 (m, 1H), 7.49 (d, J=5.4 Hz, 1H), 7.21–7.17 (m, 2H); $^{13}$C NMR (400 MHz, DMSO-d$_6$)) δ 169.2, 160.8, 159.0, 158.6, 149.6, 144.8, 140.5, 131.0, 129.9, 128.7, 128.6, 122.6, 119.6, 119.0, 115.5, 109.4; MS (TSP) m/z 331 (M+1).

Example 105

2-(3-Cyanoanilino)-4-(imidazo[1,2a]pyrid-3-yl)pyrimidine

The title compound was prepared from 4-(imidazo[1,2a]pyrid-3-yl)-2-methylthiopyrimidine and 3-aminobenzonitrile following the general method of Example 1 affording 102 mg (61% yield) of the title compound as a brown-red solid: $^1$H NMR (400 MHz, DMSO-d$_6$)) δ 10.12–10.08 (m, 2H), 8.66 (s, 1H), 8.52 (d, J=5.4 Hz, 1H), 8.38 (s, 1H), 7.97 (d, J=8.6 Hz, 1H), 7.80 (d, J=9.0 Hz, 1H), 7.58–7.43 (m, 4H), 7.19 (app t, J=6.8 Hz, 1H); $^{13}$C NMR (400 MHz, DMSO-d$_6$)) δ 160.9, 159.2, 158.9, 149.9, 143.2, 140.9, 131.9, 131.1, 129.0, 126.7, 125.5, 123.3, 122.8, 121.0, 119.3, 115.8, 113.3, 110.0; MS (TSP) m/z 313 (M+1).

Example 106

2-(3,5-Difluoroanilino)-4-(imidazo[1,2a]pyrid-3-yl) pyrimidine

The title compound was prepared from 4-(imidazo[1,2a]pyrid-3-yl)-2-methylthiopyrimidine and 3,5-difluoroaniline following the general method of Example 1. An additional purification of the product was performed by column chromatography on silica gel using chloroform/ethanol, 98:2, as the eluent affording 35 mg (20% yield) of the title compound as a pale yellow solid: $^1$H NMR (400 MHz, DMSO-d$_6$)) δ 10.11–10.09 (m, 2H), 8.66 (s, 1H), 8.52 (d, J=5.5 Hz, 1H), 7.80 (d, J=8.9 Hz, 1H), 7.59–7.51 (m, 4H), 7.18 (app t, J=6.7 Hz, 1H), 6.82–6.76 (m, 1H); $^{13}$C NMR (400 MHz, DMSO-d$_6$)) δ 161.9 (dd, J$_F$=242, J$_F$=16 Hz), 158.2, 156.5, 156.3, 147.3, 142.4 (t, J$_F$=14 Hz), 138.3, 128.5, 126.4, 120.2, 116.7, 113.1, 107.6, 100.7 (dd, J$_F$=21, J$_F$=8.5 Hz), 95.5 (t, J$_F$=26 Hz); MS (TSP) m/z 324 (M+1).

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1

4-(2-Methylimidazo[1,2a]pyrid-3-yl)-2-methylthiopyrimidine

A mixture of 3-(3-dimethylaminoprop-2-en-1-oyl)-2-methylmidazo-[1,2a]pyridine (Method 2) (20 g, 87 mmol), thiourea (6.52 g, 86 mmol) and sodium methoxide (1.19 g, 22 mmol) in butanol (220 ml) was heated at 85° C. for two hours under nitrogen. Methyl iodide (2 ml, 32 mmol) was added and the mixture heated at 85° C. for a further 1 hour. Methanol was added and the volatiles were removed by evaporation. The residue was purified by chromatography eluting with ethyl acetate/methanol (100:0 increasing in polarity to 97:3) to give the tide compound (16 g, 71% yield). NMR: 2.59 (s, 1H), 2.62 (s, 3H), 7.10 (dd, 1H), 7.40 (dd, 1H), 7.42 (d, 1H), 7.63 (d, 1H), 8.62 (s, 1H), 9.54 (d, 1H), m/z: 257 [MH]$^+$.

Method 2

3-(3-Dimethylaminoprop-2-en-1-oyl)-2-methylimidazo[1,2a]pyridine

A mixture of 3-acetyl-2-methylimidazo[1,2a]pyridine (Method 3) (40 g, 0.23 mol) and DMFDMA (200 ml) was heated at reflux under nitrogen for 4 days. The volatiles were removed by evaporation, the residue was triturated with hot diethylene ether and the solid product collected by filtration to give the title compound (21 g, 40% yield). NMR: 2.64 (s, 3H), 3.29 (s, 6H), 5.50 (d, 1H), 7.00 (dd, 1H), 7.38 (dd, 1H), 7.54 (d, 1H), 7.70 (d, 1H), 9.55 (d, 1H), m/z: 230 [MH]$^+$.

Method 3

3-Acetyl-2-methylimidazo[1,2a]pyridine

A mixture of 2-aminopyridine (60 g, 0.64 mol) and 3-chloro-2,4-pentanedione (101.4 g, 0.75 mol) in diethylene ether (450 ml) and THF (750 ml) was heated at reflux for 12 hours, then left to stand at ambient temperature for 18 hours. The solvent was removed by evaporation and the residue was purified by chromatography eluting with dichloromethane/hexane (1:1) increasing in polarity to dichloromethane/methanol (98:2). The purified product was triturated with hexane to give the title compound (46.2 g, 40% yield). NMR: 2.55 (s, 3H), 2.68 (s, 3H), 7.15 (dd, 1H), 7.56 (dd, 1H), 7.64 (d, 1H), 9.58 (d, 1H, m/z: 175 [MH]$^+$.

Method 4

4-(Imidazo[1,2a]pyrid-3-yl)-2-methylthiopyrimidine

A mixture of 3-(3-dimethylaminoprop-2-en-1-oyl)imidazo[1,2a]pyridine (Method 5) (0.90 g, 4.2 mmol), thiourea (0.32 g, 4.2 mmol) and sodium methoxide (0.34 g, 6.3 mmol) was heated at 85° C. in N-butanol (10 ml) for 2 hours. The mixture was allowed to cool to 30° C., methyl iodide (0.6 ml, 9.6 mmol) was added dropwise and stirring continued for a further 3 hours. The volatiles were removed by evaporation and the residue purified by chromatography, eluting with ethyl acetate/methanol (100:0 increasing in polarity to 97:3) to give the title compound (0.94 g, 93% yield). NMR: 2.61 (s, 3H), 7.22 (dd, 1H), 7.54 (dd, 1H), 7.72 (d, 1H), 7.77 (d, 10H. 8.56 (d, 1H), 8.66 (s, 1H), 9.83 (d, 1H); m/z: 243 [MH]$^+$.

Method 5

3-(3-Dimethylaminoprop-2-en-1-oyl)imidazo[1,2a]pyridine

A mixture of crude 3-acetylimidazo[1,2a]pyridine (Method 6) (3.3 g, 19.1 mmol) and DMFDMA (40 ml) was heated at reflux for 60 hours. The mixture was allowed to cool, the volatiles were removed by evaporation and the residue triturated with hot diethylene ether. The solid product was collected by filtration to give the title compound (2.29 g, 52% yield). NMR: 2.90 (br s, 3H), 3.10 (br s, 3H), 5.81 (d, 1H), 7.09 (dd, 1H), 7.42 (dd, 1H), 7.65 (d, 1H), 7.70 (d, 1H), 8.43 (s, 1H), 9.72 (d, 1H); m/z: 216 [MH]$^+$.

Method 6

3-Acetylimidazo[1,2a]pyridine

Aluminium chloride (20.4 g, 153.2 mmol) was added in small portions to a solution of imidazo[1,2a]pyridine (8.9 g, 75.7 mmol) in dichloromethane (150 ml) cooled at 5° C. The mixture was then allowed to warm to ambient temperature and stirred for 1 hour and then heated to reflux. Acetic anhydride (5.1 ml, 53.9 mmol) was then added slowly over 30 minutes and the mixture heated at reflux for further 90 minutes. The mixture was allowed to cool, the solvent was removed by evaporation and ice/water added to the residue. The aqueous mixture was made alkaline with 2 M aqueous sodium hydroxide solution and extracted with ethyl acetate. The combined extracts were dried and the volatiles removed by evaporation to give a brown oil. This oil was shown to consist of ~35% of the title compound, the remainder being imidazo[1,2a]pyridine. This mixture was used without further purification. NMR: 2.57 (s, 3H), 7.22 (dd, 1H), 7.61 (dd, 1H), 7.79 (d, 1H), 8.60 (s, 1H), 9.52 (d, 1H).

Method 7

4-(3,5-Dioxapineridin-1-yl)sulphonylaniline

A mixture of 1-(3,5-dioxapiperidin-1-yl)sulphonyl-4-nitrobenzene (Method 8) (500 mg, 1.82 mmol) and 10% palladium on charcoal catalyst (150 mg) in ethanol (25 ml) and ethyl acetate (25 ml) was stirred under an atmosphere of hydrogen for 3 hours. The catalyst was removed by filtration through diatomaceous earth and the filter pad was washed with ethanol and ethyl acetate. The volatiles were removed from the filtrate by evaporation and the residue triturated with diethyl ether and hexane to give the title compound (395 mg, 88% yield). NMR: 4.90 (s, 2H), 5.10 (s, 4H), 6.02 (s, 2H), 6.58 (d, 2H), 7.50 (d, 2H).

Method 8

1-(3,5-Dioxapiperidin-1-yl)sulphonyl-4-nitrobenzene

4-Nitrobenzenesulphonamide (2.02 g, 10 mmol) was added to a solution of 1,3,5-trioxane (1.96 g, 20 mmol) in acetic acid (5 ml). The mixture was stirred for 5 minutes and methanesulphonic acid (10 ml) was added slowly. The mixture was then stirred at 35° C. for 20 minutes, cooled to 0° C., diluted with water and extracted with ethyl acetate. The combined extracts were washed twice with water and twice with 5% aqueous sodium hydrogen carbonate solution, and then dried and the volatiles removed by evaporation. The residue was recrystallized from ethanol to give the title compound (955 mg, 35% yield). NMR: 4.87 (s, 2H), 5.30 (s, 4H), 8.20 (d, 2H), 8.42 (d, 2H).

Method 9

4-(2-Diethylaminoethoxy)aniline

A mixture of 4-(2-diethylaminoethoxy)-1-nitrobenzene (Method 10) (1.0 g, 4.2 mmol) and 10% palladium on charcoal catalyst (200 mg) in ethanol (30 ml) was stirred under an atmosphere of hydrogen for 3 hours. The catalyst was removed by filtration through diatomaceous earth and the filter pad was washed with methanol. The volatiles were removed from the filtrate by evaporation to give the title compound (400 mg, 46% yield) as an oil. M/z: 209 [MH]$^+$.

Method 10

4-(2-Diethylaminoethoxy)-1-nitrobenzene

Water (8 ml) and xylene (35 ml) were added to a mixture of sodium 4-nitrophenoxide (10.5 g, 65 mmol), 2-(diethylamino)ethylchloride hydrochloride (8.6 g, 50 mmol) and potassium carbonate (10.4 g, 75 mmol) and the resulting mixture was heated at reflux for 2 hours. A Dean-Stark apparatus was then fitted and the water was removed. The organic solution was allowed to cool to ambient temperature and left to stand for 18 hours. The solution was decanted from the precipitated solid and the volatiles were removed from the decanted solution by evaporation to give the title compound (8.0 g, 52% yield) as an oil. NMR: 0.90 (t, 6H), 2.50 (q, 2H), 2.89 (t, 2H), 4.15 (t, 2H), 7.15 (d, 2H), 8.18 (d, 2H); m/z: 239 [MH]$^+$.

Method 11

4-[3-(N,N-Dimethyl)amino-2-hydroxypropoxy]aniline

3-N,N-Dimethylamino-2-hydroxy-3-(4-nitrophenoxy)propane (Method 12) (3.75 g) was dissolved in ethanol (40 ml). Under an atmosphere of nitrogen, 10% palladium-on-carbon (0.4 g) was added. The nitrogen atmosphere was replaced by one of hydrogen and the reaction mixture was stirred overnight. The catalyst was removed by filtration through diatomaceous earth and the filtrate was evaporated to dryness. The residue was dissolved in diethyl diethylene ether containing a small amount of isopropanol and hydrogen chloride solution (1M in diethylene ether, 16 ml) was added. The diethylene ether was evaporated and the solid residue was suspended in isopropanol. This mixture was heated on a steam bath for several minutes then allowed to cool to ambient temperature. The resulting powder was collected by filtration, washed with isopropanol, diethylene ether and dried (3.04 g, 72.4% yield). NMR: 2.80 (s, 6H), 3.15 (m, 2H), 3.88 (m, 2H), 4.25 (m, 1H), 5.93 (br S, 1H), 6.88 (m, 4H); m/z 211 [MH]$^+$; EA $C_{11}H_{18}N_2O_2$.1.6 HCl requires C; 49.2, H; 7.4, N; 10.4, Cl; 21.7%: found: C; 49.2, H; 7.2, N; 10.1; Cl; 19.1%.

Method 12

3-N,N-Dimethylamino-2-hydroxy-1-(4-nitrophenoxy)propane 1-(4-Nitrophenoxy)-2,3-epoxypropane (Method 13) (4.3 g) was dissolved in methanol (30 ml) and N,N-dimethylformamide (10 ml). Dimethylamine (2 M solution in methanol, 17 ml) was added and the mixture was stirred at ambient temperature overnight. The reaction mixture was evaporated to dryness and the residue was dissolved in saturated sodium bicarbonate solution and ethyl acetate. The ethyl acetate layer was separated and washed twice with saturated brine, dried over anhydrous sodium sulphate, filtered and evaporated to yield an oil that slowly crystallised under high vacuum (4.79 g, 89.9% yield). NMR (CDCl$_3$): 2.33 (s, 6H), 2.98 (m, 1H), 2.54 (m, 1H), 4.00 (m, 3H), 7.00 (d, 2H), 8.20 (d, 2H); m/z 241 [MH]$^+$.

Method 13

1-(4-Nitrophenoxy)-2,3-epoxypropane 1-(4-Nitrophenoxy)-2,3-epoxypropane was prepared by an analogous method to that described by Zhen-Zhong Lui et. al. in Synthetic Communications (1994), 24, 833–838. 4-Nitrophenol (4.0 g), anhydrous potassium carbonate (8.0 g) and tetrabutylammonium bromide (0.4 g) were mixed with epibromohydrin (10 ml). The reaction mixture was heated at 100° C. for 1 hour. After cooling to ambient temperature, the reaction mixture was diluted with ethyl acetate and filtered. The filtrate was evaporated to dryness and the residue was codistilled twice with toluene. The resulting oil was purified by column chromatography and eluted with ethanol (1.0%):dichloromethane to yield on evaporation an oil that crystallised (4.36 g, 77.7% yield). NMR (CDCl$_3$): 2.78 (m, 1H), 2.95 (m, 1H), 3.38 (m, 1H), 4.02 (dd, 1H), 4.38 (dd, 1H), 7.00 (d, 2H), 8.20 (d, 2H); m/z 196 [MH]$^+$.

Method 14

2-Methylthio-4-(2,5-dimethylimidazo[1,2a]pyrid-3-yl)pyrimidine

A mixture of 3-(3-dimethylaminoprop-2-en-1-oyl)-2,5-dimethylimidazo[1,2a]pyridine (Method 15) (3.50 g, 14.4 mmol), thiourea (1.09 g, 14.4 mmol) and sodium methoxide (1.01 g, 18.7 mmol) was heated at 85° C. in 1-butanol (50 ml) for 2 hours. The mixture was allowed to cool to 30° C. and methyl iodide (1.8 ml, 28.8 mmol) was added dropwise and the mixture stirred for a further 3 hours. The volatiles were removed by evaporation and the residue purified by chromatography eluting with ethyl acetate/methanol (100:0 increasing in polarity to 97:3) to give the title compound (2.37 g, 61% yield). NMR: 2.41 (s, 3H), 2.60 (s, 3H), 2.70 (s, 3H), 7.56 (d, 1H), 7.88 (d, 1H), 7.92 (d, 1H), 8.81 (d, 1H), 9.39 (s, 1H); m/z: 271 [MH]$^+$.

Method 15

3-(3-Dimethylaminoprop-2-en-1-oyl)-2,5-dimethylimidazo[1,2,a]pyridine

A solution of 3-acetyl-2,5-dimethylimidazo[1,2,a]pyridine (Method 16) (3.60 g, 19.1 mmol) in DMFDMA (20 ml) was heated at reflux for 60 hours. The mixture was allowed to cool and the solvent was removed by evaporation. The residue was triturated with hot diethylene ether, the solid collected by filtration and dried to give the title compound (3.61 g, 84% yield). NMR: 2.30 (s, 3H), 2.62 (s, 3H), 2.90 (br s, 3H), 3.10 (br s, 3H), 5.48 (d, 1H), 7.22 (dd, 1H), 7.44 (d, 1H), 7.68 (d, 1H), 9.39 (dd, 1H).

Method 16

3-Acetyl-2,5-dimethylimidazo[1,2a]pyridine

3-Chloro-2,4-pentanedione (6.5 ml, 54.4 mmol) was added to a suspension of 2-amino-4-methylpyridine (5.00 g, 46.3 mmol) and sodium iodide (10 mg) in THF (60 ml) and the mixture was heated at reflux for 16 hours. The reaction mixture was allowed to cool and the solvent was removed by evaporation. The resulting solid residue was triturated with hot hexane, collected by filtration and dried to give the title compound (3.69 g, 43% yield). NMR: 2.35 (s, 3H), 2.75 (s, 3H), 7.41 (dd, 1H), 7.57 (d, 1H), 9.40 (d, 1H); m/z. 189 [MH]$^+$.

Method 17

4-(2-Methylpyrazolo[2,3a]pyrid-3-yl)-2-methylthiopyrimidine

A mixture of 3-(3-dimethylaminoprop-2-en-1-oyl)-2-methyl-pyrazolo[2,3a]pyridine (Method 18) (3.89 g, 17 mmol), thiourea (1.27 g, 17 mmol) and sodium methoxide (0.929 g, 17 mmol) in butanol (45 ml) was heated at 85° C. for two hours under nitrogen. Methyl iodide (1.05 ml, 17 mmol) was added and the mixture heated at 85° C. for a further 2 hours. The volatiles were removed by evaporation and the residue was purified by chromatography eluting with ethyl acetate/methanol (100:0 increasing in polarity to 97:3) to give the title compound (3.1 g, 68% yield). NMR: 2.58 (s, 1H), 2.68 (s, 3H), 7.04 (dd, 1H), 7.39 (dd, 1H), 7.48 (d, 1H), 8.35 (d, 1H), 8.50 (d, 1H), 8.72 (d, 1H); m/z: 257 [MH]$^+$.

Method 18

3-(3-Dimethylaminoprop-2-en-1-oyl)-2-methylpyrazolo[2,3a]pyridine

A mixture of 3-acetyl-2-methylpyrazolo[2,3a]pyridine (Method 19) (2 g, 11.5 mmol) and DMFDMA (10 ml) was heated 110° C. under nitrogen for 48 hours. The volatiles were removed by evaporation, the residue was triturated with hot diethylene ether and the solid product collected by filtration to give the title compound (1.98 g, 75% yield). NMR: 2.60 (s, 3H), 3.30 (s, 6H), 5.49 (d, 1H), 6.95 (dd, 1H), 7.38 (dd, 1H), 7.62 (d, 1H), 8.10 (d, 1H), 8.62 (d, 1H); m/z: 230 [MH]$^+$.

Method 19

3-Acetyl-2-methylpyrazolo[2,3a]pyridine

Potassium carbonate (53.8 g, 0.39 mol) and then 2,4-pentanedione (24.8 g, 0.25 mol) were added to a solution of 1-aminopyridinium iodide (26.9 g, 0.12 mol) in water (336 ml) and the mixture was heated at 80° C. for 2 hours, allowed to cool to ambient temperature and is left to stand for 18 hours. Water was added and the mixture was extracted to with ethyl acetate. The combined extracts were dried and the volatiles were removed by evaporation. The residue was recrystallized from hot hexane and the product collected by filtration. Solvent was removed from the filtrate by evaporation and was added to the insoluble residue from the recrystallization. This crude mixture was purified by chromatography eluting with dichloromethane/hexane (1:1) increasing in polarity to dichloromethane/methanol (97:3). This product was triturated with hexane and added to the product obtained from the initial recrystallization to give the title compound (9.6 g, 0.33% yield). NMR: 2.50 (s, 3H), 2.62 (s, 3H), 7.09 (dd, 1H), 7.55 (dd, 1H), 8.12 (d, 1H), 8.72 (d, 1H); m/z: 175 [MH]$^+$.

Method 20

2-Chloro-4-(imidazo[1,2a]pyrid-3-yl)pyrimidine

A suspension of 2-hydroxy-4-(imidazo[1,2a]pyrid-3-yl)pyrimidine (Method 21; 9.92 g, 46%) in phosphoryl chloride (200 ml) and phosphorus pentachloride (11 g, 53%) was heated at reflux under nitrogen for 24 hours. Excess phosphoryl chloride was removed by evaporation, ice water was added and the mixture neutralised with 2 M aqueous sodium hydroxide solution. The aqueous mixture was extracted with ethyl acetate, dried and evaporated to give the title compound (7.42 g, 69% yield). NMR: 7.15 (dd, 1H), 7.59 (dd, 1H), 7.80 (d, 1H), 8.05 (d, 1H), 8.64 (d, 1H), 8.79 (s, 1H), 9.72 (d, 1H); m/z: 231 [MH]$^+$.

Method 21

2-Hydroxy-4-(imidazo[1,2a]pyrid-3-yl)pyrimidine

A solution of sodium nitrate (11.04 g, 0.16 mol) in water (100 ml) was added to a solution of 2-amino-4-(imidazo[1,2a]pyrid-3-yl)pyrimidine (Method 22; 11.27 g, 0.053 mol) in 70% acetic acid (330 ml) at 60° C. The mixture was heated at 60° C. for 3 hours, allowed to cool and neutralised with 5M aqueous sodium hydroxide solution, the resulting precipitate was collected by filtration, washed quickly with cold water and dried in vacuum oven at 50° C. to give the title compound (9.95 g, 89% yield). NMR: 6.98 (d, 1H), 7.12 (dd, 1H), 7.55 (dd, 1H), 7.80 (d, 1H), 7.82 (d, 1H), 8.70 (s, 1H); m/z: 213 [MH]$^+$.

Method 22

2-Amino-4-(imidazo[1,2a]pyrid-3-yl)pyrimidine

A mixture of 3-(3-dimethylaminoprop-2-en-1-oyl)imidazo[1,2a]pyridine (Method 5; 20 g, 0.093 mol), sodium methoxide (20.1 g, 0.372 mol) and guanidine hydrochloride (22.09 g, 0.233 mol) in n-butanol (1500 ml) and methanol (1000 ml) were heated at reflux for 60 hours. The resulting solution was decanted from insoluble material, the volatiles were removed by evaporation and the residue was purified by chromatography eluting with dichloromethane/methanol (97:3) to give the title compound (13 g, 67% yield). NMR: 6.78 (s, 1H), 7.15–7.05 (m, 2H), 7.45 (dd, 2H), 7.70 (d, 1H), 8.20 (d, 1H), 8.50 (s, 1H), 10.15 (d, 1H); m/z: 212 [MH]$^+$.

Method 23

4-(N-Methylsulphamoyl)aniline

Methylamine (3 ml of a 33% solution in ethanol) and then triethylamine (0.159 ml, 1.1 mmol) was added to sulphanilyl fluoride (200 mg, 1.1 mmol), and the mixture heated at 80° C. for 6 hours then at ambient temperature for 18 hours. The volatiles were removed by evaporation and the residue azeotroped with toluene to give the title compound (160 mg, 76% yield). NMR: 2.30 (s, 3H), 5.85 (s, 2H), 6.60 (d, 2H), 7.39 (d, 2H); m/z: 187 [MH]$^+$.

Method 24

4-[N-(2-Methoxyethyl)sulphamoyl]aniline

A mixture of 2-methoxyethylamine (859 mg, 11.4 mmol), sulphanilyl fluoride (1.0 g, 5.71 mmol), and triethylamine (1.72 g, 22.9 mmol) in n-butanol (15 ml) was heated at reflux for 18 hours. The mixture was allowed to cool and the volatiles were removed by evaporation. The residue was purified by chromatography eluting with ethyl acetate/hexane (50:50) increasing in polarity to (70:30) to give the title compound (860 mg, 65% yield). NMR: 2.78 (q, 2H), 3.15 (s, 3H), 3.25 (t, 2H), 5.87 (s, 2H), 6.58 (d, 2H), 7.10 (t, 1H), 7.40 (d, 2H); m/z: 231[MH]$^+$.

Method 25–26

The following compounds were prepared using the procedure of Method 24,

| Meth | Compound Name | NMR | m/z |
|---|---|---|---|
| 25 | 4-(N-Propylsulphamoyl)aniline | 0.78(t, 3H), 1.40–1.25 (m, 2H), 2.60(q, 2H), 5.84(s, 2H), 6.59(d, 2H), 7.00(t, 1H), 7.39(d, 2H) | |
| 26 | 4-(N-Cyclopropylsulphamoyl)aniline | 0.01–0.15(m, 4H), 1.70–1.75(m, 1H), 5.60(s, 2H), 6.30(d, 2H), 7.05 (s, 1H), 7.10(d, 2H) | 211 [M-H]- |

Method 27

1-[3-(4-Bromobenzoylamino)propyl]imidazole 1-(3-Aminopropyl)imidazole (2.39 ml, 0.02 mol) was added to a solution of 4-bromobenzoyl chloride (4.0 g, 0.018 mol) in ethanol (250 ml). The mixture was stirred at ambient temperature for 18 hours. The volatiles were removed by evaporation and the residue was purified by chromatography eluting with hexane/dichloromethane (50:50) increasing in polarity to dichloromethane/methanol (80:20) to give the title compound. NMR: 1.95 (m, 2H), 3.20 (q, 2H), 4.0 (t, 2H), 6.87 (s, 1H), 7.19 (s, 1H), 7.64 (d, 2H), 7.68 (s, 1H), 7.78 (d, 2H), 8.58 (t, 1H); m/z: 308 [MH]$^+$.

Method 28

1-[3-(4-Bromobenzoylamino)propyl]-2-oxopyrolidine 1-(3-Aminopropyl)-2-oxopyrolidine (3.07 ml 14 mmol) was treated as described in Method 27 to give the title compound. NMR: 1.68 (quin, 2H), 1.90 (quin, 2H), 2.0 (t, 2H), 3.15–3.22 (m, 4H), 3.29–3.33 (m, 2H), 7.64 (d, 2H), 7.78 (d, 2H), 8.48 (t, 1H).

Method 29

2,4-Dichloro-1-(2-methoxyethylsulphamoyl)benzene 2,4-Dichlorobenzenesulphonyl chloride (500 mg 2.1 mmol) and 2-methoxyethylamine (230 mg, 3.1 mmol) in n-butanol (10 ml) was heated at reflux for one hour. The volatiles were removed by evaporation and residue purified by chromatography eluting with hexane/ethyl acetate (50:

50) to give the title compound. NMR: 3.04 (t, 2H), 3.08 (s, 3H), 3.22 (t, 2H), 7.60 (dd, 1H), 7.82 (d, 1H), 7.92 (d, 1H), 8.0 (s, 1H); m/z: 282 [M−H]⁻.

Method 30

2,4-Dichloro-1-(1-propylsulphamoyl)benzene 2,4-Dichlorobenzenesulphonyl chloride (500 mg 2.1 mmol) and 1-propylamine (0.2 ml, 2.4 mmol) in n-butanol (10 ml) was heated at reflux for 48 hours. The volatiles were removed by evaporation and the residue triturated with diethylene ether and the product collected by filtration to give the title compound. NMR: 0.78 (t, 3H), 1.35 (q, 2H), 2.79 (t, 2H), 7.60 (dd, 1H), 7.84 (d, 1H), 7.92 (d, 2H)

Method 31

2-Amino-5-bromo-4-(imidazo[1,2a]pyrid-3-yl)pyrimidine

Bromine (54 ml, 0.0011 mmol) was added dropwise to a solution of 2-amino-4-(imidazo[1,2a]pyrid-3-yl)pyrimidine (Method 22; 200 mg, 0.95 mmol) in acetic acid (4 ml) at ambient temperature. The mixture was heated at 65° C. for 90 minutes and allowed to cool. The resulting precipitate was collected by filtration, washed with hexane and dried to give the title compound. NMR: 7.44 (dd, 1H), 7.90–8.00 (m, 2H), 8.59 (s, 1H), 8.99 (s, 1H), 9.78 (d, 1H); m/z: 290 [MH]⁺.

Method 32

5-Bromoimidazo[1,2a]pyridine

A solution of bromoacetaldehyde diethylapetyl (50 ml, 0.332 mol) in dioxane (143 ml), water (85 ml) and conc. hydrochloric acid (5 ml) was heated at reflux for 30 minutes and the mixture allowed to cool. Sodium hydrogen carbonate (53 g) was added followed by a solution of 5-bromo-2-aminopyridine (30 g, 0.174 mol) in dioxane (230 ml) and water (85 ml) and the mixture was heated at reflux for 24 hours. The mixture was allowed to cool, poured into water and acidified with 2 M hydrochloric acid. The mixture was washed with ethyl acetate and the aqueous layer was basified with 2 M aqueous sodium hydroxide solution. The aqueous mixture was extracted with ethyl acetate. The extracts were combined, dried and the volatiles removed by evaporation. The residue was purified by chromatography eluting with hexane/ethyl acetate (50:50) in creasing in polarity (25:50) to give the title compound (20 g, 59% yield). NMR: 7.30 (dd, 1H), 7.54 (d, 1H), 7.59 (s, 1H), 7.90 (s, 1H), 8.89 (s, 1H); m/z: 197 [MH]⁺.

Method 33

3-Acetyl-5-bromoimidazo[1,2a]pyridine

Aluminium chloride (10.2 g, 77 mmol) was added in portions over 10 minutes to a solution of 5-bromoimidazo [1,2a]pyridine (Method 32; 5.0 g, 26 mmol) in dichloromethane (100 ml) cooled to 0° C. The mixture was heated to reflux and acetyl chloride (2.54 ml, 36 mmol) was added over 15 minutes. The mixture was heated at reflux for 24 hours, cooled to 0° C., and further aluminium chloride (10.2 g, 77 mmol) followed by acetyl chloride (3.26 ml) were added. The mixture heated at reflux for 24 hours and then the volatiles were removed by evaporation. Iced water was added, the mixture was basified with 2 M aqueous sodium hydroxide solution and extracted with ethyl acetate. The extracts were washed with water, dried and the solvent evaporated to the title compound, which was used without further purification (4.0 g). NMR: 2.58 (s, 3H), 7.74–7.82 (m, 2H), 8.62 (s, 1H), 9.62 (s, 1H); m/z: 241 [MH]⁺

Method 34

5-Bromo-3-(3-dimethylaminoprop-2-en-1-oyl)imidazo[1,2a]pyridine

3-Acetyl-5-bromoimidazo[1,2a]pyridine (Method 33; 4.0 g) was dissolved in DMFDMA (200 ml) and the mixture was heated at reflux under nitrogen for 72 hours. The excess DMFDMA was removed by evaporation and the residue triturated with hot diethylene ether, collected by filtration and washed with diethylene ether to give the title compound (2.6 g, 53% yield). NMR: 2.90 (s, 3H), 3.12 (s, 1H), 5.82 (d, 1, H), 7.58 (dd, 1H), 7.64 (d, 1H), 7.70 (s, 1H), 8.44 (s, 1H), 9.90 (s, 1H); m/z: 294 [MH]⁺.

Method 35

2-Amino-4-(5-bromoimidazo[1,2a]pyrid-3-yl)pyrimidine

A mixture of 5-bromo-3-(3-dimethylaminoprop-2-en-1-oyl)imidazo[1,2a]pyridine (Method 34; 2.5 g, 8.5 mmol) guanidine hydrochloride (2.01 g, 21 mmol) and sodium methoxide (1.83 g, 34 mmol) in n-butanol(140 ml) and methanol (45 ml) was heated at reflux for 18 hours. The volatiles were removed by evaporation and the residue purified by chromatography eluting with dichloromethane/ methanol (95:5) to give the title compound (1.1 g, 45% yield). NMR: 6.86 (s, 2H), 7.12 (d, 1H), 7.57 (dd, 1H), 7.68 (d, 1H), 8.22 (d, 1H), 8.51 (s, 1H); m/z: 290 [MH]⁺.

Method 36

6-Phenylimidazo[1,2a]pyridine

2-Amino-4-phenylpyridine (0.90 g, 5.29 mmol) was treated as described in Method 32 to give the title compound. NMR: 7.07 (d, 1H), 7.35–7.53 (m, 4H), 7.59 (s, 1H), 7.64 (d, 2H), 7.83 (s, 1H), 8.18 (d, 1H); m/z: 195 [MH]⁺.

Method 37

3-Bromo-6-phenylimidazo[1,2a]pyridine

A solution of bromine (0.24 ml, 4.6 mmol) in water (10 ml) was added to a solution of 6-phenylimidazo[1,2a]pyridine (Method 36; 0.85 g, 4.88 mmol) in ethanol (15 ml) and the mixture stirred for 14 hours in the dark. The mixture was basified with aqueous sodium hydrogen carbonate solution and extracted with dichloromethane. The extracts were dried, the solvent removed by evaporation and the residue triturated with diethylene ether and collected by filtration to give the title compound. NMR: 7.38–7.56 (m, 4H), 7.77 (s, 1H), 7.83 (d, 2H), 7.96 (s, 1H), 8.39 (d, 1H); m/z: 273 [MH]⁺.

Method 38

3-(3-Dimethylaminoprop-2-en-1-oyl)-6-phenylimidazo[1,2a]pyridine

Phenylmagnesium bromide (2.7 ml of a 1M solution in THF) was added to a solution of 3-bromo-6-phenylimidazo[1,2a]pyridine (Method 37; 0.48 g, 1.76 mmol) in THF under nitrogen and the mixture was heated at reflux for 2 hours. The mixture was cooled to 0° C. and N-methoxy-N-methylacetamide (0.3 ml 2.64 mmol) was added dropwise. The mixture was allowed to warm to ambient temperature and stirred for 18 hours. The reaction mixture was diluted with diethylene ether, washed with aqueous sodium hydrogen carbonate solution, then brine dried and the volatiles removed by evaporation. The residue was dissolved in DMFDMA (10 ml) and the mixture heated at reflux under nitrogen for 60 hours. The excess DMFDMA was removed by evaporation and the residue triturated with hot diethylene ether, collected by filtration and washed with diethylene ether to give the title compound (170 mg, 33% yield). NMR: 2.8–3.2 (br d, 6H), 5.85 (d, 1H), 7.38–7.58 (m, 4H), 7.67 (d, 1H), 7.86 (d, 2H), 8.00 (s, 1H), 8.48 (s, 1H), 9.76 (d, 1H); m/z: 292 [MH]$^+$.

Method 39

3-(3-Dimethylaminoprop-2-en-1-oyl)-2-methyl-6-methoxyimidazo[1,2a]pyridine

3-Acetyl-6-methoxy-2-methylimidazo[1,2a]pyridine (Method 40; 1.49 g, 7.3 mmol) and toluenesulphonic acid (5 mg) in DMFDMA (25 ml) was heated at reflux for 20 hours. The excess DMFDMA was removed by evaporation. The residue was triturated with diethylene ether and the product collected by filtration to give the title compound. NMR: 2.69 (s, 3H), 3.28 (s, 6H), 3.82 (s, 3H), 5.44 (d, 1H), 6.69 (dd, 1H), 6.97 (d, 1H), 7.65 (d, 1H), 9.21 (d, 1H); m/z: 260 [MH]$^+$.

Method 40

3-Acetyl-6-methoxy-2-methylimidazo[1,2a]pyridine

A solution of 3-chloroacetoacetone (2.86 ml) in THF (6 ml) was added to a solution of 2-amino-4-methoxypyridine (2.71 g, 21.8 mmol) in THF (14 ml) and the mixture was stirred at ambient temperature for 30 minutes and then heated at reflux for 3 hours. The solvent was removed by evaporation and the residue purified by chromatography eluting with dichloromethane/methanol (100:0) increasing in polarity to (97:3). The product was recrystallized from tert-butylmethyl diethylene ether to give the title compound (2.1 g, 47% yield). NMR: 2.05 (s, 3H), 2.63 (s, 3H), 3.86 (s, 3H), 6.83 (dd, 1H), 7.07 (d, 1H), 9.20 (d, 1H); m/z: 205 [MH]$^+$.

Method 41

4-Sulphamoylphenylguanidine

A mixture of sulphanilamide (20 g, 0.166 mol), benzoyl cyanamide (34 g, 0.33 mol) in ethanol (60 ml) and concentrated hydrochloric acid (11 ml) was heated on a steam bath until the solvent had evaporated. Water was added and the mixture heated at reflux for 5 minutes. Sodium hydroxide (14.4 g) was added and the mixture heated at reflux. The mixture was allowed to cool and was adjusted to pH2 with hydrochloric acid and the precipitated solid removed by filtration. The filtrate was neutralised and the solvent removed by evaporation. The residue was recrystallized from water to give the crude title product. m/z: 215 [MH]$^+$.

Method 42

4-(2-Diethylaminoethoxy)phenylguanidine

A mixture of 3,5-dimethylpyrazolylformidinium nitrate (0.20 g, 1 mmol), 4-(2-diethylaminoethoxy)aniline Method 9; 1.0 g, 4.8 mmol) in water (1 ml) was heated at reflux for 3 hours. The solvent was removed by evaporation, the residue triturated with hot diethylene ether and the product collected by filtration to give crude title compound. NMR: 0.98 (t, 6H), 2.57 (q, 4H), 2.79 (t, 2H), 4.00 (t, 2H), 6.99 (d, 2H), 7.15 (d, 2H); m/z: 251 [MH]$^+$.

Pharmaceutical Formulations

According to one aspect of the present invention there is provided a pharmaceutical formulation comprising a compound of formula (I), as a free base or a pharmaceutically acceptable salt thereof, for use in the treatment and/or prophylaxis of conditions associated with glycogen synthase kinase-3 inhibition.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream or for rectal administration as a suppository.

In general the above compositions may be prepared in a conventional manner using conventional excipients.

Suitable daily doses of the compounds of formula (I) in the treatment of a mammal, including man are approximately 0.01 to about 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

The following illustrate representative pharmaceutical dosage forms containing a compound of formula (I), as a free base or a pharmaceutically acceptable salt thereof (hereafter compound X), for therapeutic or prophylactic use in mammals:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

-continued

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

The above formulations may be obtained by conventional procedures well known in the pharmaceutical art.

Medical Use

We have found that the compounds defined in the present invention, as a free base or a pharmaceutically acceptable salt thereof, are well suited for inhibiting glycogen synthase kinase-3 (GSK3). Accordingly, the compounds of the present invention are expected to be useful in the treatment and/or prophylaxis of conditions associated with glycogen synthase kinase-3 activity, i.e. the compounds may be used to produce an inhibitory effect of GSK3 in mammals, including man in need of such treatment and/or prophylaxis.

GSK3 is highly expressed in the central and peripheral nervous system and in other tissues. Thus, it is expected that a compound of the invention is well suited for the treatment and/or prophylaxis of conditions associated with glycogen synthase kinase-3 activity in the central and peripheral nervous system. In particular, such compounds of the invention are expected to be suitable for treatment and/or prophylaxis of conditions associated with especially, dementia, Alzheimer's Disease, Parkinson's Disease, Frontotemporal dementia Parkinson's Type, Parkinson dementia complex of Gaum, HIV dementia, diseases with associated neurofibrillar tangle pathologies, amyotrophic lateral sclerosis, corticobasal degeneration, dementia pugilistica, Down's Syndrome, Huntington's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, Type I and Type II Diabetes and Diabetic neuropathy, hair loss and contraceptive medication.

The dose required for the therapeutic or prophylactic treatment of a particular disease will necessarily be varied depending on the host treated, the route of administration and the severity of the illness being treated.

Non-Medical Use

In addition to their use in therapeutic medicine, the compounds of formula (I), as a free base or pharmaceutically salts are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutical agents.

Pharmacology

Determination of ATP Competition in Scintillation Proximity GSK3β Assay

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (AstraZeneca, Lund), was added at a final concentration of 1 μM in an assay buffer containing 1 mU recombinant human GSK3β (Dundee University, UK), 12 nM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 μg BSA/25 μl. The reaction was initiated by the addition of 0.04 μCi [$\gamma$-$^{33}$P]ATP (Amersham, UK) and unlabelled ATP at a final concentration of 1 μM and assay volume of 25 μl. After incubation for 20 minutes at room temperature, each reaction was terminated by the addition of 25 μl stop solution containing 5 mM EDTA, 50 μM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 μM.

| MOPS | Morpholinepropanesulfonic acid |
|---|---|
| EDTA | Ethylendiaminetetraaceticacid |
| BSA | Bovin Serum Albumin |
| ATP | Adenosine Triphosphate |
| SPA | Scintillation Proximity Assay |
| GSK3 | Glycogen synthase kinase 3 |

RESULTS

Typical $K_i$ values for the compounds of the present invention are in the range of about 0.001 to about 10,000 nM. Other values for $K_i$ are in the range of about 0.001 to about 1000 nM. Further values for $K_i$ are in the range of about 0.001 nM to about 300 nM.

What is claimed is:

1. A method of treatment of conditions associated with glycogen synthase kinase-3 activity selected from the group consisting of dementia, Alzheimer's disease, Parkinsons disease, Frontotemporal dementia Parkinson's type, Parkinson's dementia complex of Guam, HIV dementia, mayotropic lateral sclerosis, corticobasal degeneration, dementia puglistica, postencephalitic Parkinsonism, progressive supranuclear palsy, Pick's disease, Nieman Pick's disease, Bipolar disease, depression, cognitive disorders, Type I and Type II diabetes, diabetic retinopathy and hairloss comprising administering to a mammal in need of such treatment a therapeutically effective amount of a compound of formula (I)

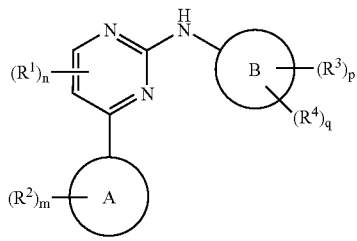

or a pharmaceutically acceptable salt thereof wherein:

Ring A is imidazo[1,2a]pyrid-3-yl or pyrazolo[2,3a]pyrid-3-yl, $R^2$ is attached to a ring carbon and is selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{3-6}$cycloalkyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0, 1, or 2, $C_{1-6}$alkoxycarbonyl, N-($C_{1-6}$alkyl)sulphamoyl, N,N-($C_{1-6}$alkyl)$_2$sulphamoyl, phenyl, heterocyclic group, phenylthio and, (heterocyclic group)thio; wherein any $C_{1-6}$alkyl, $C_{2-6}$alkenyl, $C_{2-6}$alkynyl, phenyl or heterocyclic group may be optionally substituted on carbon by one or more G; and wherein if said heterocyclic group contains an —NH— moiety that nitrogen may be optionally substituted by a group selected from Q;

m is 0, 1, 2, 3, 4 or 5; wherein the values of $R^2$ may be the same or different;

$R^1$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-2}$alkyl)$_2$amino, $C_{1-3}$alkanoylamino, N-($C_{1-3}$alkyl)carbamoyl, N,N-($C_{1-2}$ alkyl)$_2$ carbamoyl, $C_{1-3}$ alkylS(O)$_a$ wherein a is 0, 1 or 2, N-($C_{1-3}$ alkyl)sulphamoyl or N,N-($C_{1-3}$alkyl)$_2$sulphamoyl; wherein any $C_{1-2}$alkyl, $C_{1-3}$alkyl, $C_{2-3}$alkenyl or $C_{2-3}$alkynyl may be optionally substituted on carbon by one or more J;

n is 0, 1 or 2, wherein the values of $R^1$ may be the same or different;

Ring B is phenyl or phenyl fused to a $C_{5-7}$cycloalkyl ring;

$R^3$ is halo, nitro, cyano, hydroxy, amino, carboxy, carbamoyl, mercapto, sulphamoyl, $C_{1-6}$alkyl, $C_{2-6}$alkenyl, $C_{2-6}$alkynyl or $C_{1-6}$alkoxy;

p is 0, 1, 2, 3 or 4; wherein the values of $R^3$ may be the same or different;

$R^4$ is a group A-E-; wherein

A is selected from hydrogen, $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl; which $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl may be optionally substituted on carbon by one or more D; and wherein if said heterocyclic group contains an —NH— moiety, that nitrogen may be optionally substituted by a group selected from R;

E is a direct bond or —O—, —C(O)—, —OC(O)—, —C(O)O—, —N($R^a$)C(O)—, —C(O)N($R^a$)—, —N($R^a$)—, —S(O)$_r$—, —SO$_2$N($R^a$)— or —N($R^a$)SO$_2$—; wherein $R^a$ is hydrogen or $C_{1-6}$alkyl optionally substituted by one or more D and r is 0, 1 or 2;

D is independently selected from oxo, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_1$ alkylS(O)$_a$ wherein a is 0 to 2, $C_{1-6}$alkoxycarbonyl, $C_{1-6}$alkoxycarbonylamino, benzyloxycarbonylamino, N-($C_{1-6}$alkyl)sulphamoyl and N,N-($C_{1-6}$ alkyl)$_2$sulphamoyl; wherein any $C_{1-6}$alkyl, $C_{2-6}$alkenyl, $C_{2-6}$alkynyl or phenyl may be optionally substituted on carbon by one or more K;

q is 0, 1 or 2; wherein the values of $R^4$ maybe the same or different; and wherein p+q≦5;

G, J and K are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl; and Q and R are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl) carbamoyl, benzyl, benzyloxycarbonyl, benzoyl and phenylsulphonyl.

2. The method according to claim 1, wherein the condition is dementia or Alzheimer's Disease.

3. A compounds selected from the group consisting of
2-(4-Fluoro-3-methylanilino)-4-(imidazo[1,2a]pyrid-3-yl)pyrimidine,
2-(4-Cyanoanilino)-4-(imidazo[1,2a]pyrid-3-yl)pyrimidin,
2-(4-Chloroanilino)-4-(imidazo[1,2a]pyrid-3-yl)pyrimidine,
2-Anilino-4-(2-methylimidazo[1,2a]pyrid-3-yl)pyrimidine,
2-[4-(Pyrimid-2-ylaminosulphonyl)anilino]-4-(imidazo[1,2a]pyrid-3-yl)pyrimidine,
2-(4-Carbamoylanilino)-4-(imidazo[1,2a]pyrid-3-yl)pyrimidine,
2-(3-Cyanoanilino)-4-(imidazo[1,2a]pyrid-3-yl)pyrimidine,
2-(3,5-Difluoroanilino)-4-(imidazo[1,2a]pyrid-3-yl)pyrimidine,
2-(3-Chloroanilino)-4-(imidazo[1,2a]pyrid-3-yl)pyrimidine,
2-[4-(N,N-Dimethyl-carbamoyl)anilino]4-(imidazo[1,2a]pyrid-3-yl)primidine,
2-(4-Mesylanilino)-4-(imidazo[1,2a]pyrid-3-yl)pyrimidine and 2-(3-Sulphamoylanilino)-4-(imidazo[1,2a]pyrid-3-yl)pyrimidine,
and a pharmaceutically acceptable salt of any one of said compounds.

4. A pharmaceutical formulation comprising a therapeutically effective amount of a compound of formula (I) as defined in claim 1 or a pharmaceuticaly acceptable salt thereof and conventional excipients.

5. The pharmaceutical formulation according to claim 4, wherein the compound is selected from the group consisting of
2-(4-Fluoro-3-methylanilino)-4-(imidazo[1,2a]pyrid-3-yl)pyrimidine,
2-(4-Cyanoanilino)-4-(imidazo[1,2a]pyrid-3-yl)pyrimidine,
2-(4-Chloroanilino)-4-(imidazo[1,2a]pyrid-3-yl)pyrimidine,
2-Anilino-4-(2-methylimidazo[1,2a]pyrid-3-yl)pyrimidine,
2-[4-(Pyrimid-2-ylaminosulphonyl)anilino]-4-(imidazo[1,2a]pyrid-3-yl)pyrimidine,
2-(4-Carbamoylanilino)-4-(imidazo[1,2a]pyrid-3-yl)pyrimidine,
2-(3-Cyanoanilino)-4-(imidazo[1,2a]pyrid-3-yl)pyrimidine,
2-(3,5-Difluoroanilino)-4-(imidazo[1,2a]pyrid-3-yl)pyrimidine,
2-(3-Chloroanilino)-4-(imidazo[1,2a]pyrid-3-yl)pyrimidine,
2-[4-(N,N-Dimethyl-carbamoyl)anilino]4-(imidazo[1,2a]pyrid-3-yl)primidine,
2-(4-Mesylanilino)-4-(imidazo[1,2a]pyrid-3-yl)pyrimidine and
2-(3-Sulphamoylanilino)-4-(imidazo[1,2a]pyrid-3-yl)pyrimidine, and a pharmaceutically acceptable salt of any one of said compounds.

6. A method for inhibition of glycogen synthase kinase-3 comprising administering to a mammal a therapeutically effective amount of a compound of formula (I)

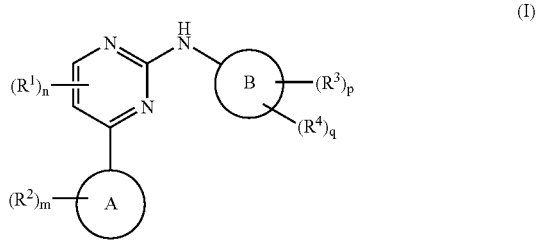

(I)

or a pharmaceutically acceptable salt thereof wherein:
Ring A is imidazo[1,2a]pyrid-3-yl or pyrazolo[2,3a]pyrid-3-yl,
$R^2$ is attached to a ring carbon and is selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{3-6}$cycloalkyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0, 1, or 2, $C_{1-6}$alkoxycarbonyl, N-($C_{1-6}$alkyl)sulphamoyl, N,N-($C_{1-6}$alkyl)$_2$sulphamoyl, phenyl, heterocyclic group, phenylthio and, (heterocyclic group)thio; wherein any $C_{1-6}$alkyl, $C_{2-6}$alkenyl, $C_{2-6}$alkynyl, phenyl or heterocyclic group may be optionally substituted on carbon by one or more G; and wherein if said heterocyclic group contains an —NH— moiety that nitrogen may be optionally substituted by a group selected from Q;
m is 0, 1, 2, 3, 4 or 5; wherein the values of $R^2$ may be the same or different;
$R^1$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-3}$alkyl)$_2$amino, $C_{1-3}$alkanoylamino, N-($C_{1-3}$alkyl)carbamoyl, N,N-($C_{1-2}$ alkyl)$_2$ carbamoyl, $C_{1-3}$ alkylS(O)$_a$ wherein a is 0, 1 or 2, N-($C_{1-3}$alkyl)sulphamoyl or N,N-($C_{1-3}$alkyl)$_2$sulphamoyl; wherein any $C_{1-2}$alkyl, $C_{1-3}$alkyl, $C_{2-3}$alkenyl or $C_{2-3}$alkynyl may be optionally substituted on carbon by one or more J;
n is 0, 1 or 2, wherein the values of $R^1$ may be the same or different;
Ring B is phenyl or phenyl fused to a $C_{5-7}$cycloalkyl ring;
$R^3$ is halo, nitro, cyano, hydroxy, amino, carboxy, carbamoyl, mercapto, sulphamoyl, $C_{1-6}$alkyl, $C_{2-6}$alkenyl, $C_{2-6}$alkynyl or $C_{1-6}$alkoxy;
p is 0, 1 2, 3 or 4; wherein the values of $R^3$ may be the same or different;
$R^4$ is a group A-E-; wherein
A is selected from hydrogen, $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl; which $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl may be optionally substituted on carbon by one or more D; and wherein if said heterocyclic group contains an —NH— moiety, that nitrogen may be optionally substituted by a group selected from R;
E is a direct bond or —O—, —C(O)—, —OC(O)—, —C(O)O—, —N($R^a$)C(O)—, —C(O)N($R^a$)—, —N($R^a$)—, —S(O)$_r$—, —SO$_2$N($R^a$)— or —N($R^a$)SO$_2$—; wherein $R^a$ is hydrogen or $C_{1-6}$alkyl optionally substituted by one or more D and r is 0, 1 or 2;
D is independently selected from oxo, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_1$ alkylS(O)$_a$ wherein a is 0 to 2, $C_{1-6}$alkoxycarbonyl, $C_{1-6}$alkoxycarbonylamino, benzyloxycarbonylamino, N-($C_{1-6}$alkyl)sulphamoyl and N,N-($C_{1-6}$ alkyl)$_2$sulphamoyl; wherein any $C_{1-6}$alkyl, $C_{2-6}$alkenyl, $C_{2-6}$alkynyl or phenyl may be optionally substituted on carbon by one or more K;
q is 0, 1 or 2; wherein the values of $R^4$ maybe the same or different; and wherein p+q≦5;
G, J and K are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N- dimethylsulphamoyl, N,N-diethylsulphamoyl and N-methyl-N-ethylsulphamoyl; and

Q and R are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl) carbamoyl, benzyl, benzyloxycarbonyl, benzoyl and phenylsulphonyl.

7. The method according to claim 6, wherein the compound is selected from the group consisting of 2-(4-Fluoro-3-methylanilino)-4-(imidazo[1,2a]pyrid-3-yl)pyrimidine, 2-(4-Cyanoanilino)-4-(imidazo[1,2a]pyrid-3-yl)pyrimidine, 2-(4-Chloroanilino)-4-(imidazo[1,2a]pyrid-3-yl)pyrimidine, 2-Anilino-4-(2-methylimidazo[1,2a]pyrid-3-yl)pyrimidine, 2-[4-(Pyrimid-2-ylaminosulphonyl)anilino]-4-(imidazo [1,2a]pyrid-3-yl)pyrimidine, 2-(4-Carbamoylanilino)-4-(imidazo[1,2a]pyrid-3-yl)pyrimidine, 2-(3-Cyanoanilino)-4-(imidazo[1,2a]pyrid-3-yl)pyrimidine, 2-(3,5-Difluoroanilino)-4-(imidazo[1,2a]pyrid-3-yl)pyrimidine, 2-(3-Chloroanilino)-4-(imidazo[1,2a]pyrid-3-yl)pyrimidine, 2-[4-(N,N-Dimethyl-carbamoyl)anilino]4-(imidazo[1,2a] pyrid-3-yl)primidine, 2-(4-Mesylanilino)-4-(imidazo[1,2a]pyrid-3-yl)pyrimidine and 2-(3-Sulphamoylanilino)-4-(imidazo[1,2a]pyrid-3-yl)pyrimidine, and a pharmaceutically acceptable salt of any one of said compounds.

8. A method for contraception comprising administering to a male mammal a therapeutically effective amount of a compound of formula (I)

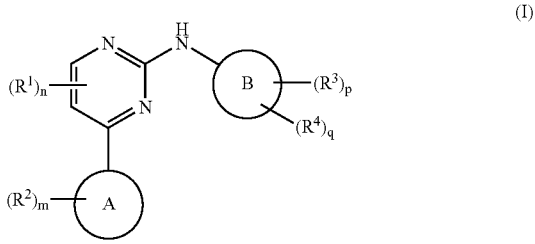

(I)

or a pharmaceutically acceptable salt thereof wherein:

Ring A is imidazo[1,2a]pyrid-3-yl or pyrazolo[2,3a]pyrid-3-yl, $R^2$ is attached to a ring carbon and is selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{3-6}$cycloalkyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0, 1, or 2, $C_{1-6}$alkoxycarbonyl, N-($C_{1-6}$alkyl)sulphamoyl, N,N-($C_{1-6}$alkyl)$_2$sulphamoyl, phenyl, heterocyclic group, phenylthio and, (heterocyclic group)thio; wherein any $C_{1-6}$alkyl, $C_{2-6}$alkenyl, $C_{2-6}$alkynyl, phenyl or heterocyclic group may be optionally substituted on carbon by one or more G; and wherein if said heterocyclic group contains an —NH— moiety that nitrogen may be optionally substituted by a group selected from Q;

m is 0, 1, 2, 3, 4 or 5; wherein the values of $R^2$ may be the same or different;

$R^1$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-2}$alkyl)$_2$amino, $C_{1-3}$alkanoylamino, N-($C_{1-3}$alkyl) carbamoyl, N,N-($C_{1-2}$alkyl)$_2$carbamoyl, $C_{1-3}$ alkylS (O)$_a$ wherein a is 0, 1 or 2, N-($C_{1-3}$alkyl)sulphamoyl or N,N-($C_{1-3}$alkyl)$_2$sulphamoyl; wherein any $C_{1-2}$alkyl, $C_{1-3}$alkyl, $C_{2-3}$alkenyl or $C_{2-3}$alkynyl may be optionally substituted on carbon by one or more J;

n is 0, 1 or 2, wherein the values of $R^1$ may be the same or different;

Ring B is phenyl or phenyl fused to a $C_{5-7}$cycloalkyl ring;

$R^3$ is halo, nitro, cyano, hydroxy, amino, carboxy, carbamoyl, mercapto, sulphamoyl, $C_{1-6}$alkyl, $C_{2-6}$alkenyl, $C_{2-6}$alkynyl or $C_{1-6}$alkoxy;

p is 0, 1 2, 3 or 4; wherein the values of $R^3$ may be the same or different;

$R^4$ is a group A-E-; wherein

A is selected from hydrogen, $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl; which $C_{1-6}$alkyl, phenyl, a heterocyclic group, $C_{3-8}$cycloalkyl, phenyl$C_{1-6}$alkyl, (heterocyclic group) $C_{1-6}$alkyl or $C_{3-8}$cycloalkyl$C_{1-6}$cycloalkyl may be optionally substituted on carbon by one or more D; and wherein if said heterocyclic group contains an —NH— moiety, that nitrogen may be optionally substituted by a group selected from R;

E is a direct bond or —O—, —C(O)—, —OC(O)—, —C(O)O—, —N($R^a$)C(O)—, —C(O)N($R^a$)—, —N($R^a$)—, —S(O)$_r$—, —SO$_2$N($R^a$)— or —N($R^a$) SO$_2$—; wherein $R^a$ is hydrogen or $C_{1-6}$alkyl optionally substituted by one or more D and r is 0, 1 or 2;

D is independently selected from oxo, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_1$ alkylS(O)$_a$ wherein a is 0 to 2, $C_{1-6}$alkoxycarbonyl, $C_{1-6}$alkoxycarbonylamino, benzyloxycarbonylamino, N-($C_{1-6}$ alkyl)sulphamoyl and N,N-($C_{1-6}$ alkyl)$_2$sulphamoyl; wherein any $C_{1-6}$alkyl, $C_{2-6}$alkenyl, $C_{2-6}$alkynyl or phenyl may be optionally substituted on carbon by one or more K;

q is 0, 1 or 2; wherein the values of $R^4$ maybe the same or different; and wherein p+q≦5;

G, J and K are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl; and Q and R are independently selected from C$_{1-4}$alkyl, C$_{1-4}$alkanoyl, C$_{1-4}$alkylsulphonyl, C$_{1-4}$alkoxycarbonyl, carbamoyl, N-(C$_{1-4}$alkyl)carbamoyl, N,N-(C$_{1-4}$alkyl) carbamoyl, benzyl, benzyloxycarbonyl, benzoyl and phenylsulphonyl.

9. The method according to any one of claims 8, wherein the compound is selected from the group consisting of
- 2-(4-Fluoro-3-methylanilino)-4-(imidazo[1,2a]pyrid-3-yl)pyrimidine,
- 2-(4-Cyanoanilino)-4-(imidazo[1,2a]pyrid-3-yl)pyrimidine,
- 2-(4-Chloroanilino)-4-(imidazo[1,2a]pyrid-3-yl)pyrimidine,
- 2-Anilino-4-(2-methylimidazo[1,2a]pyrid-3-yl)pyrimidine,
- 2-[4-(Pyrimid-2-ylaminosulphonyl)anilino]-4-(imidazo[1,2a]pyrid-3-yl)pyrimidine,
- 2-(4-Carbamoylanilino)-4-(imidazo[1,2a]pyrid-3-yl)pyrimidine,
- 2-(3-Cyanoanilino)-4-(imidazo[1,2a]pyrid-3-yl)pyrimidine,
- 2-(3,5-Difluoroanilino)-4-(imidazo[1,2a]pyrid-3-yl)pyrimidine,
- 2-(3-Chloroanilino)-4-(imidazo[1,2a]pyrid-3-yl)pyrimidine,
- 2-[4-(N,N-Dimethyl-carbamoyl)anilino]4-(imidazo[1,2a]pyrid-3-yl)primidine,
- 2-(4-Mesylanilino)-4-(imidazo[1,2a]pyrid-3-yl)pyrimidine and
- 2-(3-Sulphamoylanilino)-4-(imidazo[1,2a]pyrid-3-yl)pyrimidine, and a pharmaceutically acceptable salt of any one of said compounds.

10. The method according to any one of claim 1 or 2, wherein the compound is selected from the group consisting of
- 2-(4-Fluoro-3-methylanilino)-4-(imidazo[1,2a]pyrid-3-yl)pyrimidine,
- 2-(4-Cyanoanilino)-4-(imidazo[1,2a]pyrid-3-yl)pyrimidine,
- 2-(4-Chloroanilino)-4-(imidazo[1,2a]pyrid-3-yl)pyrimidine,
- 2-Anilino-4-(2-methylimidazo[1,2a]pyrid-3-yl)pyrimidine,
- 2-[4-(Pyrimid-2-ylaminosulphonyl)anilino]-4-(imidazo[1,2a]pyrid-3-yl)pyrimidine,
- 2-(4-Carbamoylanilino)-4-(imidazo[1,2a]pyrid-3-yl)pyrimidine,
- 2-(3-Cyanoanilino)-4-(imidazo[1,2a]pyrid-3-yl)pyrimidine,
- 2-(3,5-Difluoroanilino)-4-(imidazo[1,2a]pyrid-3-yl)pyrimidine,
- 2-(3-Chloroanilino)-4-(imidazo[1,2a]pyrid-3-yl)pyrimidine,
- 2-[4-(N,N-Dimethyl-carbamoyl)anilino]4-(imidazo[1,2a]pyrid-3-yl)primidine,
- 2-(4-Mesylanilino)-4-(imidazo[1,2a]pyrid-3-yl)pyrimidine and
- 2-(3-Sulphamoylanilino)-4-(imidazo[1,2a]pyrid-3-yl)pyrimidine, and a pharmaceutically acceptable salt of any one of said compounds.

* * * * *

UNITED STATES PATENT AND TRADEMARK OFFICE
CERTIFICATE OF CORRECTION

| | |
|---|---|
| PATENT NO. | : 7,078,410 B2 |
| APPLICATION NO. | : 10/468605 |
| DATED | : July 18, 2006 |
| INVENTOR(S) | : Berg et al. |

It is certified that error appears in the above-identified patent and that said Letters Patent is hereby corrected as shown below:

<u>TITLE PAGE, ITEM (57) ABSTRACT</u>: replace the entire ABSTRACT with the following ABSTRACT:
--The present invention relates to a new use of pyrimidine derivatives of formula (I), as a free base or a pharmaceutically acceptable salt thereof in the manufacture of a medicament in the treatment and/or prophylaxis of conditions associated with glycogen synthase kinase-3.

The present invention further relates to a method of treatment and/or prophylaxis of conditions associated with glycogen synthase kinase-3, comprising administrating to a mammal, including man in need of such prevention and/or prophylaxis a therapeutically effective amount of said pyrimidine derivatives, as well as a pharmaceutical formulation for said use. In addition, the present invention relates to new compounds suitable for the inhibition of glycogen synthase kinase-3.--

<u>Col. 52, line 64</u>: "Parkinsons" should read --Parkinson's--.

<u>Col. 52, lines 66 and 67</u>: "mayotropic" should read --amyotrophic--.

<u>Col. 53, line 2</u>: "Nieman Pick's" should read --Niemann-Pick's--.

<u>Col. 53, line 4</u>: "retinopathy and hairloss" should read --neuropathy and hair loss--.

<u>Col. 53, line 39</u>: delete "selected from".

<u>Col. 53, lines 40, 52 and 58</u>: "the values of" should read --each--.

<u>Col. 54, line 4</u>: delete "selected from".

<u>Col. 54, line 16</u>: "$C_1 alkylS(O)_a$" should read --$C_{1-6}alkylS(O)_a$--.

UNITED STATES PATENT AND TRADEMARK OFFICE
CERTIFICATE OF CORRECTION

PATENT NO. : 7,078,410 B2
APPLICATION NO. : 10/468605
DATED : July 18, 2006
INVENTOR(S) : Berg et al.

It is certified that error appears in the above-identified patent and that said Letters Patent is hereby corrected as shown below:

Col. 54, line 23: "the values of $R^4$ maybe" should read --each $R^4$ may be--.

Col. 54, line 45: "compounds" should read --compound--.

Col. 54, line 49: "din," should read -dine,--.

Col. 56, lines 4 and 35: delete "selected from".

Col. 56, lines 5, 17 and 23: "the values of" should read --each--.

Col. 56, line 47: "C1 alkylS(O)$_a$" should read --$C_{1-6}$alkylS(O)$_a$--.

Col. 56, line 54: "the values of $R^4$ maybe" should read --each $R^4$ may be--.

Col. 58, lines 3 and 34: delete "selected from".

Col. 58, lines 4, 16 and 22: "the values of" should read --each--.

Col. 58, line 46: "$C_1$ alkylS(O)$_a$ should read --$C_{1-6}$alkylS(O)$_a$--.

Col. 58, line 53: "the values of $R^4$ maybe" should read --each $R^4$ may be--.

Col. 59, line 6: "any one of claims" should read --claim--.

UNITED STATES PATENT AND TRADEMARK OFFICE
CERTIFICATE OF CORRECTION

| | |
|---|---|
| PATENT NO. | : 7,078,410 B2 |
| APPLICATION NO. | : 10/468605 |
| DATED | : July 18, 2006 |
| INVENTOR(S) | : Berg et al. |

It is certified that error appears in the above-identified patent and that said Letters Patent is hereby corrected as shown below:

Col. 60, line 1: delete "any one of".

Signed and Sealed this

Fifth Day of December, 2006

JON W. DUDAS
*Director of the United States Patent and Trademark Office*